(12) United States Patent
Ishida et al.

(10) Patent No.: US 11,352,501 B2
(45) Date of Patent: Jun. 7, 2022

(54) ANTHOCYANIN-BASED PIGMENT COMPOSITION

(71) Applicant: SAN-EI GEN F.F.I., INC., Toyonaka (JP)

(72) Inventors: Masahiko Ishida, Tsu (JP); Takayoshi Ohara, Tsu (JP); Nobuko Fukino, Tsu (JP); Tomohiro Kakizaki, Tsu (JP); Tomomichi Ohno, Tsu (JP); Koji Hamasaki, Toyonaka (JP); Takamasa Yokoyama, Toyonaka (JP); Masashi Imai, Toyonaka (JP)

(73) Assignee: SAN-EI GEN F.F.I., INC., Toyonaka (JP)

( * ) Notice: Subject to any disclaimer, the term of this patent is extended or adjusted under 35 U.S.C. 154(b) by 719 days.

(21) Appl. No.: 15/506,587

(22) PCT Filed: Aug. 26, 2015

(86) PCT No.: PCT/JP2015/074127
§ 371 (c)(1),
(2) Date: Feb. 24, 2017

(87) PCT Pub. No.: WO2016/031887
PCT Pub. Date: Mar. 3, 2016

(65) Prior Publication Data
US 2017/0253744 A1 Sep. 7, 2017

(30) Foreign Application Priority Data
Aug. 26, 2014 (JP) .............................. JP2014-172089

(51) Int. Cl.
| C09B 61/00 | (2006.01) |
| A23L 5/43 | (2016.01) |
| A23L 2/58 | (2006.01) |
| A61K 47/46 | (2006.01) |
| A61K 47/26 | (2006.01) |
| A61K 8/60 | (2006.01) |
| A61K 8/9789 | (2017.01) |

(52) U.S. Cl.
CPC .............. *C09B 61/00* (2013.01); *A23L 2/58* (2013.01); *A23L 5/43* (2016.08); *A61K 8/60* (2013.01); *A61K 8/9789* (2017.08); *A61K 47/26* (2013.01); *A61K 47/46* (2013.01); *A23V 2002/00* (2013.01)

(58) Field of Classification Search
CPC ... C09B 61/00; A23L 2/58; A23L 5/42; A61K 8/60; A61K 47/46; A61K 47/26; A61K 8/97
See application file for complete search history.

(56) References Cited

U.S. PATENT DOCUMENTS

| 6,180,154 | B1 | 1/2001 | Wrolstad et al. | |
| 2003/0124235 | A1* | 7/2003 | Yukawa | C09B 61/00 |
| | | | | 426/540 |
| 2011/0251408 | A1* | 10/2011 | Mathews | A01H 4/00 |
| | | | | 549/406 |

FOREIGN PATENT DOCUMENTS

| EP | 1 293 539 A1 | 3/2003 |
| JP | 59-223756 A | 12/1984 |
| JP | 61-36364 A | 2/1986 |
| JP | 61-97361 A | 5/1986 |
| JP | 61-97362 A | 5/1986 |
| JP | 61-101560 A | 5/1986 |
| JP | 4-154871 A | 5/1992 |
| JP | 10-36701 A | 2/1998 |
| JP | 2000-290525 A | 10/2000 |
| JP | 2004-75911 A | 3/2004 |
| JP | 2007060992 A * | 3/2007 |
| JP | 2013-198436 A | 10/2013 |
| JP | 2014-161319 A | 9/2014 |
| WO | 01/90254 A1 | 11/2001 |

OTHER PUBLICATIONS

Ishida, M., Kakizaki, T., Morimitsu, Y., Ohara, T., Hatakeyama, K., Yoshiaki, H., Kohori, J., Nishio, T. 2015. Novel glucosinolate composition lacking 4-methylthio-3-buentyl glucosinolate in Japanese white radish (Raphanus sativus L.). Theor. Appl. Genet. vol. 128, pp. 2037-2046.*

Jing, P., Ruan, S.-Y., Dong, Y., Zhang, X.-G., Yue, J., Kan, J.-Q., Slavin, M., Yu, L. 2011. "Optimization of purification conditions of radish (Raphanus sativus L.) anthocyanin-rich extracts using chitosan." Food Sci. Tech. vol. 44, pp. 2097-2103.*

Rodriguez-Saona, L.E., Guisti, M.M., Wrolstead, R.E. 1998. "Anthocyanin Pigment Composition of Red-Fleshed Potatoes." J. Food Sci. vol. 63, pp. 458-465.*

Mori, M., Kayashi, K., Ohara-Takada, A., Watanuki, H., Katahira, R., Ono, H., Terahara, N. 2010. "Anthocyanins from Skins and Fleshes of Potato Varieties." Food Sci. Technol. Res. vol. 16, pp. 115-122.*

(Continued)

*Primary Examiner* — Nikki H. Dees
(74) *Attorney, Agent, or Firm* — Sughrue Mion, PLLC

(57) ABSTRACT

Provided is an anthocyanin pigment composition having the following features:
(A) an aqueous solution containing the composition and adjusted to pH of 3 with a citrate buffer (pH: 3.0) has a maximum absorption wavelength of 500 to 550 nm in the visible light region; (B) when a pigment-composition-containing aqueous solution containing the composition, 0.2 mass % citric acid, 20 mass % ethanol, and water is prepared so as to have a color value $E^{10\%}_{1\ cm}$ of 10, 1 mL of the aqueous solution is sealed in a 20-mL vial, and the vial is stored at 50° C. for 5 days and further maintained at 40° C. for 30 minutes, the total amount of methyl mercaptan, dimethyl disulfide, and dimethyl trisulfide in the gas in the sealed space of the vial is 100 pg/mL or less; and (C) the gas in the sealed space of the vial contains 5-methylthiopentanenitrile when the vial is maintained at 40° C. for 30 minutes in (B) above.

3 Claims, 6 Drawing Sheets

(56) References Cited

OTHER PUBLICATIONS

Ishida et al., "Chemical changes of the breakdown compounds of glucosinolate in processed food of the daikon without containing 4-methylthio-3-butenyl glucosinolate : Toward the development of manufacturing products of daikon without both sulfurous odors and yellow pigments," Journal of Japan Association on Odor Environment, vol. 44, No. 5, Sep. 15, 2013 pp. 307-314.
Shokuhin kagaku shinbun [Food chemistry newspaper], Jan. 16, 2014, No. 2518, p. 3.
International Search Report of PCT/JP2015/074127, dated Dec. 1, 2015 (PCT/ISA/210).
Communication dated Jan. 2, 2018 from the European Patent Office in counterpart application No. 15836862.1.
Gao et al., "Removal of off-flavours from radish (*Raphanus sativus* L.) anthocyanin-rich pigments using chitosan and its mechanism(s)", Food Chemistry, vol. 146, 2014, pp. 423-428.
Gauche et al., "Effect of pH on the copigmentation of anthocyanins from Cabernet Sauvignon grape extracts with organic acids", Sci. Agric. (Piracicaba, Braz.), vol. 67, No. 1, Jan./Feb. 2010, pp. 41-46.
Harborne et al., "Spectral Methods of Characterizing Anthocyanins", Biochemical Journal, vol. 70., 1958, pp. 22-28.
Giusti et al., "Anthocyanin Pigment Composition of Red Radish Cultivars as Potential Food Colorants", Journal of Food Science, vol. 63, No. 2, 1998, pp. 219-224.

\* cited by examiner

ANTHOCYANIN-BASED PIGMENT COMPOSITION

CROSS REFERENCE TO RELATED APPLICATIONS

This is a U.S. national stage of application No. PCT/JP2015/074127, filed on Aug. 26, 2015. Priority under 35 U.S.C. § 119(a) and 35 U.S.C. § 365(b) is claimed from Japanese Patent Application No. 2014-172089 filed on Aug. 26, 2014, the disclosure of which is incorporated herein by reference.

TECHNICAL FIELD

The present invention relates to a high-quality anthocyanin pigment composition that can be provided more efficiently and at a lower cost than red cabbage pigment, the composition having color development characteristics, heat resistance, and light resistance that are equivalent to or better than those of red cabbage pigment.

BACKGROUND ART

Anthocyanin pigments, which are natural pigments derived from natural products, are in increased demand as a result of consumers' recent preference for natural products.

Of these, red cabbage pigment, because of its hues ranging from red to purple and excellent light resistance, heat resistance, and color development, has been reported to be the anthocyanin pigment most in demand. This is statistically shown: for example, in Japan, the demand for red cabbage pigment per year in fiscal 2013 was 120 t/year, which was higher than that of other anthocyanin pigments such as purple sweet potato pigment (70 t/year), purple corn pigment (55 t/year), and red radish pigment (34 t/year) (see NPL 1).

Proposed techniques related to a method for producing red cabbage pigment include a method wherein a pigment extract of red cabbage or the like is purified with a cation exchange resin or an adsorption resin, and treated using an ultrafiltration membrane (PTL 1); a method wherein a pigment extract of red cabbage or the like is subjected to cation exchange treatment, treatment with an ultrafiltration membrane, and adsorption treatment with silica gel (PTL 2); a method wherein polyphosphate, titanate, or tannin and/or tannic acid was added to a red cabbage pigment extract (water or alcohol solution) to remove impurities in the pigment (PTL 3 to 5); a method wherein a pigment extract such as red cabbage pigment is treated with an anion exchange resin (PTL 6); a method wherein an adsorption resin to which a water-soluble natural pigment is adsorbed is brought into contact with subcritical or supercritical carbon dioxide (PTL 7); a method wherein treatment using a microorganism such as a yeast or a mold is performed during or after extraction of a natural pigment (PTL 8); a method wherein an adsorption-treated solution of an extract of red cabbage or the like is subjected to adsorption treatment etc., and acid treatment at 40° C. or more (PTL 9); and the like.

CITATION LIST

Patent Literature

PTL 1: JPS59-223756A
PTL 2: JPS61-036364A
PTL 3: JPS61-097361A
PTL 4: JPS61-101560A
PTL 5: JPS61-097362A
PTL 6: JPH4-154871A
PTL 7: JPH10-036701A
PTL 8: JP2000-290525A
PTL 9: JP2004-075911A

Non-Patent Literature

NPL 1: Shokuhin kagaku shinbun [Food chemistry newspaper], Jan. 16, 2014, No. 2518, p. 3

SUMMARY OF INVENTION

Technical Problem

However, red cabbage, which is a raw material of red cabbage pigment, does not have high productivity as a crop. More specifically, red cabbage, a headed vegetable, requires a relatively long cultivation period, and is thus susceptible to weather etc. Additionally, red cabbage is not easy to cultivate. For these reasons, red cabbage has problematic production efficiency, which makes it difficult to obtain the raw material inexpensively.

Red cabbage pigment is advantageous in that since it has less odor than other anthocyanin pigments, it can be used in a wide variety of foods and beverages even if the degree of purification and deodorization is low. However, there is a problem such that odor derived from the raw material affects the flavor depending on the form of the food or beverage.

Performing the steps shown in PTL 1 to 9 for purification and deodorization of the pigment leads to a further increase in production costs.

Therefore, an object of the present invention is to provide a high-quality anthocyanin pigment composition more efficiently and at a lower cost than red cabbage pigment, which has not been achieved by the prior art.

Solution to Problem

In view of the problems described above, the present inventors focused on a new attempt to seek an anthocyanin pigment that could be an alternative to red cabbage pigment. The inventors conducted extensive research, and surprisingly found that the use of an anthocyanin-pigment-containing colored radish exhibiting 4-methylthio-3-butenyl glucosinolate (hereinafter, may be referred to as "4MTB-GSL") deficiency as a raw material makes it possible to obtain an anthocyanin pigment composition having a "smell component composition similar to that of red cabbage," which cannot be found in hitherto known colored radishes.

More specifically, the inventors found that the composition of the main smell components of the anthocyanin pigment composition is similar to that of red cabbage pigment. That is, the inventors found that although the anthocyanin pigment composition is derived from "radish," because it emits a slight rapeseed-like smell like red cabbage pigment and has good smell quality and weak smell intensity, it does not cause any problems for general use in, for example, foods and beverages (e.g., use with other flavors etc.).

The inventors conducted further extensive research on the anthocyanin pigment composition, and found that the pigment composition has excellent color development characteristics, heat resistance, and light resistance that are equivalent to or better than those of red cabbage pigment. In particular, regarding color development characteristics, the inventors found that a pigment composition having hues in a wide range of orange-red to purple in an acidic range can be prepared by varying the type of anthocyanin-pigment-containing colored radish used as a raw material.

In contrast, only a pigment composition exhibiting hues ranging from red to purple in an acidic range can be obtained from red cabbage; a pigment composition that can exhibit hues ranging from orange-red to red cannot be obtained.

The inventors also found that the anthocyanin pigment composition is a composition in which the "sulfur odor" particular to Brassicaceae plant pigments is significantly suppressed. The inventors found that a pigment composition can be obtained that is free of the most disliked odor components, described as "stuffy odor," i.e., "dimethyl disulfide" and "dimethyl trisulfide," among sulfur odor; or that contains these components in significantly reduced amounts. The inventors also found that the anthocyanin pigment composition undergoes significantly reduced generation of "return smell" (a phenomenon also called "odor regression") after long-term storage at high temperature.

Specifically, the inventors found that the anthocyanin pigment composition can be used as an alternative to red cabbage pigment for, for example, foods and beverages, even when it is not purified or deodorized.

The inventors also found that since radish used as a raw material can be stably cultivated and has high production efficiency, the pigment composition can be very easily prepared in large quantities.

The present invention is highly creative in that the inventors focused on using a specific "radish" as a raw material to solve the new problem of an alternative to red cabbage pigment, and found that a high-quality anthocyanin pigment that has a smell component composition similar to that of red cabbage pigment and in which odor is significantly suppressed can be obtained.

The present invention has been accomplished based on the above findings and, specifically, relates to the following anthocyanin pigment compositions.

Item 1.

An anthocyanin pigment composition derived from a plant other than red cabbage (or whose raw material is a plant other than red cabbage) (or obtained from a plant other than red cabbage), the composition having the following features (A), (B), and (C):
(A) an aqueous solution containing the anthocyanin pigment composition and adjusted to a pH of 3 with a citrate buffer (pH: 3.0) has a maximum absorption wavelength in the range of 500 to 550 nm in the visible light region;
(B) when a pigment-composition-containing aqueous solution containing the anthocyanin pigment composition, 0.2 mass % citric acid, 20 mass % ethanol, and water is prepared so as to have a color value $E^{10\%}_{1cm}$ of 10, 1 mL of the aqueous solution is sealed in a 20-mL vial, and the vial is stored at 50° C. for 5 days and further maintained at 40° C. for 30 minutes, the total amount of methyl mercaptan, dimethyl disulfide, and dimethyl trisulfide in the gas in the sealed space of the vial is 100 pg/mL or less; and (C) the gas in the sealed space of the vial contains 5-methylthiopentanenitrile when the vial is maintained at 40° C. for 30 minutes in (B) above.

Item 2.

The anthocyanin pigment composition according to Item 1, further having the following feature (D):
(D) the total mass of dimethyl disulfide and dimethyl trisulfide in the gas in the sealed space of the vial is less than or equal to five times the mass of methyl mercaptan in the gas in the sealed space when the vial is maintained at 40° C. for 30 minutes in (B) above.

Item 3.

The anthocyanin pigment composition according to Item 1 or 2, which is an extract or squeezed juice of an anthocyanin-pigment-containing colored radish exhibiting 4-methylthio-3-butenyl glucosinolate deficiency (or an extract or squeezed juice obtained from an anthocyanin-pigment-containing colored radish exhibiting 4-methylthio-3-butenyl glucosinolate deficiency).

Item 4.

An anthocyanin pigment composition comprising an extract or squeezed juice of an anthocyanin-pigment-containing colored radish exhibiting 4-methylthio-3-butenyl glucosinolate deficiency (or an extract or squeezed juice obtained from an anthocyanin-pigment-containing colored radish exhibiting 4-methylthio-3-butenyl glucosinolate deficiency).

Item 5.

The anthocyanin pigment composition according to Item 3 or 4, wherein the anthocyanin-pigment-containing colored radish is a radish having a 4-methylthio-3-butenyl glucosinolate-deficient trait due to the same or substantially the same genetic factor as that of a cultivar "Daikon Radish Parental Line No. 5."

Item 6.

An anthocyanin pigment composition that is the anthocyanin pigment composition according to any one of Items 1 to 5 that has been purified and/or deodorized (or that is obtained by subjecting the anthocyanin pigment composition according to any one of Items 1 to 5 to purification and/or deodorization treatment).

The present invention also relates to the following pigment preparation.

Item 7.

A pigment preparation comprising the anthocyanin pigment composition according to any one of Items 1 to 6.

The present invention also relates to the following methods for producing an anthocyanin pigment composition.

Item 8.

A method for producing an anthocyanin pigment composition, comprising extracting an anthocyanin pigment from an anthocyanin-pigment-containing colored radish exhibiting 4-methylthio-3-butenyl glucosinolate deficiency.

Item 9.

The method according to Item 8, wherein the anthocyanin pigment composition is the anthocyanin pigment composition according to any one of Items 1 to 6.

Item 10.

A method for producing an anthocyanin pigment composition, comprising squeezing juice from an anthocyanin-pigment-containing colored radish exhibiting 4-methylthio-3-butenyl glucosinolate deficiency.

Item 11.

The method according to Item 10, wherein the anthocyanin pigment composition is the anthocyanin pigment composition according to any one of Items 1 to 6.

Advantageous Effects of Invention

The present invention makes it possible to provide a high-quality anthocyanin pigment composition that can be an alternative to red cabbage pigment, more efficiently and at a lower cost than red cabbage pigment.

More specifically, the present invention makes it possible to provide an anthocyanin pigment composition, derived from a natural raw material, that has color development characteristics, heat resistance, and light resistance equivalent to or better than those of red cabbage pigment and in which sulfur odor and return smell thereof are significantly suppressed. Therefore, deterioration of quality because of return smell can be prevented in the pigment composition and products colored with the pigment composition.

The present invention also makes it possible to provide a pigment composition exhibiting hues in a very wide range compared with the hues that red cabbage pigment can exhibit.

DESCRIPTION OF EMBODIMENTS

Figure 1:
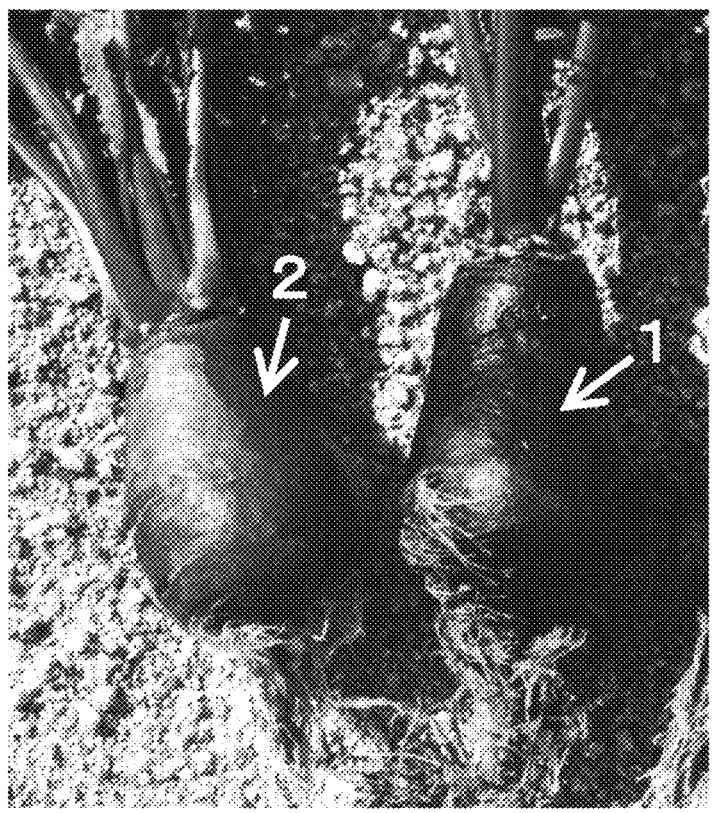
FIG. 1 shows photographs of 4MTB-GSL-deficient colored radishes produced in the production of raw material radish lines of Example 1. (A): Photographic image of appearance of each enlarged root portion (root and hypocotyl portion). (B): Photographic image of the cross-section cut of each enlarged root portion. Reference numeral 1: 4MTB-GSL deficient purple colored radish. Reference numeral 2: 4MTB-GSL deficient red colored radish.
Figure 1:
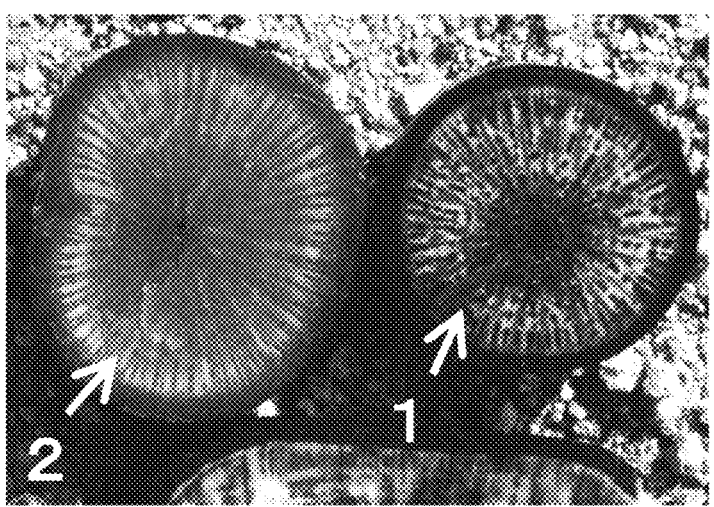

Hereinafter, embodiments of the present invention are described in detail.

Terms

As used herein, "smell" refers to a stimulus that is emitted from an object and that is perceived by the nose.

As used herein, "odor" refers to an unpleasant smell.

As used herein, "flavor," unless specifically limited, refers to taste, smell, or a combination thereof.

As used herein, "citrate buffer" is a buffer prepared using citric acid and phosphate ($Na_2HPO_4$), and is also known as a McIlvaine buffer.

As used herein, "citrate buffer (pH: 3.0)" refers to a buffer adjusted to a pH of 3.0 using citric acid and phosphate ($Na_2HPO_4$). More specifically, "citrate buffer (pH 3.0)" can be prepared according to the method described in Japan's Specifications and Standards for Food Additives, 8th ed. (Ministry of Health, Labour and Welfare, Japan).

As used herein, the "maximum absorption wavelength" (λmax) of the pigment composition refers to the light wavelength (nm) at which absorbance is maximum in the visible light region. As used herein, "absorbance" refers to a value indicating how much light a substance absorbs. For example, absorbance ($A_\lambda$) at the maximum absorption wavelength (λmax) can be determined using the following (Equation 1), wherein A represents absorbance, λ represents the maximum absorption wavelength, $A_\lambda$ represents absorbance at the maximum absorption wavelength, I represents incident light intensity, and $I_0$ represents transmitted light intensity.

$$A=-\log_{10}(I/I_0) \qquad \text{(Equation 1)}$$

As used herein, "color value" means "color value $E^{10\%}_{1cm}$." "Color value $E^{10\%}_{1cm}$" is a value calculated by measuring absorbance (A) at the maximum absorption wavelength (λmax) in the visible light region using a measurement cell having an optical path length of 1 cm when a 10% (w/v) pigment composition-containing solution is prepared. "Color value $E^{10\%}_{1cm}$" may be referred to as "color value (10% E)." More specifically, the color value can be calculated according to the method described in Japan's Specifications and Standards for Food Additives, 8th ed. (Ministry of Health, Labour and Welfare).

As used herein, "vial" refers to a sample bottle having hermeticity capable of forming a sealed space. More specifically, as the "vial," a vial formed from a material that is usable for storage of volatile components (e.g., a vial made of glass) can be used. In the present specification, allowing a vial to stand in a thermostatic bath can be employed as a means of maintaining a vial at 40° C., or storing a vial at a high temperature.

As used herein, "red cabbage pigment" is a pigment composition containing cyanidin acylglycoside(s), which are anthocyanin pigment, as main component, and is obtained by extraction from red cabbage leaves using a weak acid aqueous solution. "Red cabbage" as used herein is cabbage having a high anthocyanin pigment content (*Brassica oleracea* var. *capitata* DC), which is also called purple cabbage or murasaki kanran. Red cabbage is a plant also known as "purple cabbage," and purple cabbage is another name for red cabbage. These are merely different names for the same plant.

1. Anthocyanin Pigment Composition

The present invention relates to a high-quality anthocyanin pigment composition having color development characteristics, heat resistance, and light resistance that are equivalent to or better than those of red cabbage pigment, and the anthocyanin pigment composition can be provided more efficiently and at a lower cost than red cabbage pigment.

Usability of Brassicaceae Plant Pigments

An example of a pigment obtained using a Brassicaceae plant as a raw material is red cabbage pigment, which contains anthocyanin pigment(s) derived from a natural raw material. Red cabbage pigment has excellent heat resistance and light resistance, exhibits a wide range of hues from red to purple, and further has good color development characteristics. Because of these excellent properties, red cabbage pigment is expected to be widely used as a coloring agent for coloring products that the human body ingests, such as foods and beverages. The anthocyanin pigments of Brassicaceae plants have unique colors that cannot be developed with other pigments such as grape juice pigment, elderberry pigment, and purple corn pigment (purple corn pigment), and have excellent characteristics.

However, pigments derived from Brassicaceae plants have the problem of the particular "sulfur odor" that originates from the sulfur compounds of the Brassicaceae plants used as raw materials. The sulfur odor is a serious problem when using Brassicaceae plants as raw materials of pigments.

Sulfur compounds, which are odor components of the sulfur odor, are substances for which humans have an extremely low perception threshold sensitivity; thus, even in a very small amount, it is a substance that is perceived as an offensive odor. The sulfur odor adversely affects, in particular, the flavor and fragrance of products, such as foods, beverages, and cosmetics, making it difficult to use Brassicaceae plant pigments in general fields.

The most serious problem is, for example, "odor regression" or "return smellreturn smell." "Odor regression" is a phenomenon in which odor becomes stronger when a pigment composition is subjected to heat treatment (e.g., during production, processing, and cooking) or over time (e.g., storage), and its odor is called "return smellreturn smell."

The "return smellreturn smell" is difficult to completely avoid (it is difficult to obtain a pigment composition that is free of or almost free of the return smellreturn smell), even when an extract of a pigment raw material is purified and deodorized; therefore, it is the most difficult to resolve when using Brassicaceae plant pigments as pigment materials.

Among Brassicaceae plants, "red cabbage" is a raw material plant with a relatively low degree of sulfur odor derived from the raw material. Even if the purification degree is low, suitable pigment preparations that can be used in a wide variety of foods and beverages can be obtained using red cabbage. Accordingly, "red cabbage" has drawn attention as a pigment raw material in the food industry (NPL 1).

As described above, red cabbage pigment is recognized as a pigment material that is extremely useful as a natural pigment. However, even red cabbage pigment has the inherent problem particular to Brassicaceae plant raw materials such that it contains causative substances of sulfur odor. In particular, the problem of "return smell" caused by heat treatment or over time is a factor limiting applications of the pigment.

Methods for purifying and deodorizing red cabbage pigment or the like that have been proposed include those disclosed in PTL 1 to 9. Although red cabbage pigment preparations produced using these techniques have reduced odor compared with untreated ones, there are many cases in which the problem of "return smell" cannot be completely resolved, depending on the degree of purification and deodorization steps.

The deodorization effect can be expected to be improved by performing purification and deodorization steps in multiple stages; however, this decreases the yield because of loss of the pigment components in the steps, and requires equipment, labor, time, etc., causing a serious problem in production costs. Additionally, performing enzyme treatment or microbial treatment causes the new problem of contamination with foreign substances (need for removal).

Red cabbage pigment also has another problem such that the productivity of the raw material of the pigment, i.e., red cabbage as a crop, is not high.

Color Development Characteristics of Pigment Composition

The pigment composition according to the present invention has color development characteristics that are equivalent to or better than those of red cabbage pigment, because of the properties of the anthocyanin pigments constituting the composition.

More specifically, the pigment composition according to the present invention has the following feature:

(A) An aqueous solution containing the anthocyanin pigment composition and adjusted to a pH of 3 with a citrate buffer (pH: 3.0) has a maximum absorption wavelength in the range of 500 to 550 nm in the visible light region.

The pigment composition according to the present invention contains anthocyanin(s) as main pigment component.

"Anthocyanins" as used herein are pigment components that exhibit colors ranging from red to purple to blue, and that are glycosides in which sugar chains (e.g., glucose, galactose, and rhamnose) are attached to anthocyanidins. Anthocyanins also include acylated anthocyanins in which organic acids (e.g., sinapic acid, caffeic acid, succinic acid, and malonic acid) are attached to sugar chains of anthocyanins.

"Anthocyanidins" are composed of a three-ring structure, i.e., A, B, and C rings, and are classified into six main types of anthocyanidins (pelargonidin, cyanidin, delphinidin, peonidin, petunidin, and malvidin) by the numbers of hydroxy groups (—OH) and methoxyl groups (—OCH$_3$) added to the B ring. The larger the number of hydroxy groups, the more bluish the color they tend to exhibit. Pelargonidin, which has one hydroxy group, exhibits an orange-red color; cyanidin, which has two hydroxy groups, exhibits colors ranging from red-purple to purple; and delphinidin, which has three hydroxy groups, exhibits a bluish-purple color. When the hydroxy group(s) in the B ring are replaced by methoxyl group(s), the color becomes reddish.

The anthocyanin pigment(s) contained in the pigment composition according to the present invention preferably contain pelargonidin-type anthocyanin(s) and/or cyanidin-type anthocyanin(s) as main component(s). The more pelargonidin-type anthocyanin(s) the pigment composition contains, the closer to orange-red the hue of the composition in an acidic range (maximum absorption wavelength at a pH of 3: around 505 to 520 nm). On the other hand, the more cyanidin-type anthocyanins the pigment composition contains, the closer to purple the hue of the composition in an acidic range (maximum absorption wavelength at a pH of 3: around 520 to 540 nm).

The pigment composition according to the present invention preferably contains acylated anthocyanins as main anthocyanin pigments. Acylated anthocyanins are compounds that have excellent stability compared with that of other anthocyanins.

Examples of "acylated anthocyanins" include pelargonidin-acylglycosides (e.g., pelargonidin 3-sophoroside-5-glucoside), cyanidin-acylglycosides (e.g., cyanidin 3-sophoroside-5-glucoside), and the like.

Naturally, the pigment composition can contain anthocyanin pigments other than the anthocyanin pigments described above.

The pigment composition according to the present invention exhibits hues ranging from orange-red to purple in an acidic range (e.g., pH: 2 to 5). When expressed by hue values in the Munsell color system (or JIS color names), the pigment composition according to the present invention exhibits hues ranging from 10 YR (yellowish orange) to 5 YR (orange) to 10 R (yellowish red) to 5 R (red) to 10 RP (purplish red) to 5 RP (red-purple) to 10 P (reddish purple) to 5 P (purple). When expressed by the maximum absorption wavelength, the pigment composition according to the present invention has a maximum absorption wavelength in the range of 500 to 550 nm, and preferably 505 to 540 nm when an aqueous solution containing the pigment composition is adjusted to a pH of 3 with a citrate buffer (pH: 3.0).

In the present invention, whether an aqueous solution containing the anthocyanin pigment composition and adjusted to a pH of 3 with a citrate buffer (pH: 3.0) has a maximum absorption wavelength in the range of 500 to 550 nm in the visible light region can be determined by measuring the absorbance according to a usual method.

More specifically, the maximum absorption wavelength can be determined as follows: the absorbance of the aqueous solution is measured with a spectrophotometer, and the maximum absorption wavelength is determined as the wavelength value at which the obtained absorbance is maximum.

The coloration range and the maximum absorption wavelength range that can be adjusted in the pigment composition according to the present invention are broader than those of red cabbage pigment (exhibited hues: 10 RP (purplish red) to 5 RP (red purple) to 10 P (reddish purple) to 5 P (purple) in an acidic range; maximum absorption wavelength range at a pH of 3: 520 to 540 nm). Thus, the pigment composition according to the present invention allows color development in a wide hue range.

When the pigment composition according to the present invention is prepared in powder form, it becomes slightly dark in color. In a solution in the neutral to alkaline range, the hue that is exhibited changes to a bluish or greenish hue.

The pigment composition according to the present invention has heat resistance and light resistance that are equivalent to or better than red cabbage pigment. Specifically, the pigment composition according to the present invention is less likely to lose color development characteristics because of heat or light, and is thus highly stable. The extent of the stability is such that the composition has heat resistance and light resistance equivalent to or higher than anthocyanin pigments derived from other natural raw materials.

This stability is regarded to be properties such that the color development characteristics are less likely to be lost even after heat treatment (e.g., during production, processing, and cooking) or over time (e.g., storage).

As described above, the pigment composition according to the present invention has color development characteristics in which the characteristics of the anthocyanin(s) in the pigment composition enable the composition to exhibit, in addition to the hues possessed by red cabbage pigment, a wide range of hues that cannot be developed with red cabbage pigment.

Since the pigment composition according to the present invention has both excellent heat resistance and light resistance, the pigment composition according to the present invention is also regarded as excellent in preservability and processing characteristics.

Smell Characteristics of Pigment Composition
Amounts of Sulfur Odor Components Generated Sulfur compounds (sulfur odor components), which are odor components of sulfur odor that Brassicaceae plant pigments, including red cabbage pigment, have, are substances for which humans have an extremely low perception threshold sensitivity; thus, even in a very small amount, they are perceived as an offensive odor. In the pigment composition according to the present invention, generation of sulfur odor components (sulfur odor) is significantly low compared with red cabbage pigment.

The pigment composition according to the present invention is a composition in which the amounts of sulfur odor components that Brassicaceae plant pigments have are significantly reduced.

As an index for determining the amounts of sulfur odor components generated, the total amount of methyl mercaptan, dimethyl disulfide, and dimethyl trisulfide generated can be used. Since these three components are the main odor components causing the sulfur odor, whether the sulfur odor of the pigment composition is suppressed can be determined by measuring the total amount of these components.

In the pigment composition according to the present invention, the amounts of sulfur odor components generated, more specifically, the total amount of methyl mercaptan, dimethyl disulfide, and dimethyl trisulfide in the gas in the sealed space measured according to the method described in (B) below is less than or equal to a fixed amount.

Specifically, the pigment composition according to the present invention has the following feature:

(B) When a pigment-composition-containing aqueous solution containing the pigment composition according to the present invention, 0.2 mass % citric acid, 20 mass % ethanol, and water is prepared so as to have a color value $E^{10\%}_{1cm}$ of 10, 1 mL of the aqueous solution is sealed in a 20-mL vial, and the vial is stored at 50° C. for 5 days and further maintained at 40° C. for 30 minutes, the total amount of methyl mercaptan, dimethyl disulfide, and dimethyl trisulfide in the gas in the sealed space of the vial (in 19-fold volume of the gas relative to the solution) is 100 pg/mL or less, preferably 75 pg/mL or less, more preferably 50 pg/mL or less, even more preferably 20 pg/mL or less, further more preferably 10 pg/mL or less, particularly preferably 5 pg/mL or less, and further even more preferably 4.83 pg/mL or less.

The total amount of methyl mercaptan, dimethyl disulfide, and dimethyl trisulfide in the gas in the sealed space (in 19-fold volume of the gas relative to the solution) can be measured by storing the vial at 50° C. for 5 days, further maintaining the vial at 40° C. for 30 minutes, collecting the smell components present in the headspace of the vial with an SPME fiber (PDMS/DVB) for 30 minutes while maintaining the vial at 40° C., and then performing GC/MS analysis (gas chromatography mass spectrometry).

In the pigment composition according to the present invention, the total amount of dimethyl disulfide and dimethyl trisulfide in the gas in the sealed space of the vial (in 19-fold volume of the gas relative to the solution) is preferably 100 pg/mL or less, more preferably 50 pg/mL or less, even more preferably 20 pg/mL or less, still even more preferably 10 pg/mL or less, and particularly preferably 5 pg/mL or less.

Composition Ratio of Sulfur Odor Components

The pigment composition according to the present invention has a very characteristic composition ratio of odor components (composition ratio of sulfur odor components). Specifically, the ratio of the total mass of dimethyl disulfide and dimethyl trisulfide to the mass of methyl mercaptan in the sulfur odor components generated from the pigment composition is significantly low.

"Methyl mercaptan" is known as an odor component described as an onion-like odor, which is a type of sulfur odor. This sulfur odor is also described as a pickled radish odor.

On the other hand, "dimethyl disulfide" and "dimethyl trisulfide" are causative factors of "stuffy odor," which is a particularly very pungent odor among sulfur odor. In particular, "dimethyl trisulfide" is an odor component that is perceived as an extremely unpleasant bad odor. This pungent odor is disfavored especially in applications of pigment preparations.

Because of the feature of the composition ratio of the sulfur odor components, the pigment composition according to the present invention has odor characteristics such that no or almost no "stuffy odor" is generated. Moreover, the pigment composition according to the present invention has a component composition in which "stuffy odor" is less likely to be generated, even when the pigment concentration in the pigment composition is significantly increased to thereby increase the content itself of odor components.

The composition ratio of the sulfur odor components in the pigment composition according to the present invention is such that the total mass of dimethyl disulfide and dimethyl trisulfide in the gas in the sealed space measured according to the method described in (D) below is less than or equal to a fixed amount relative to the mass of methyl mercaptan in the gas in the sealed space.

Specifically, the pigment composition according to the present invention preferably has the following feature: (D) the total mass of dimethyl disulfide and dimethyl trisulfide in the gas in the sealed space of the vial is less than or equal to five times the mass of methyl mercaptan in the gas in the sealed space when the vial is maintained at 40° C. for 30 minutes in (B) above.

More specifically, when a pigment-composition-containing aqueous solution containing the pigment composition according to the present invention, 0.2 mass % citric acid, 20 mass % ethanol, and water is prepared so as to have a color value $E^{10\%}_{1cm}$ of 10, 1 mL of the aqueous solution is sealed in a 20-mL vial, and the vial is stored at 50° C. for 5 days and further maintained at 40° C. for 30 minutes, the total amount of dimethyl disulfide and dimethyl trisulfide in the gas in the sealed space of the vial (in 19-fold volume of the gas relative to the solution) is less than or equal to 5 times, preferably less than or equal to 2 times, more preferably less than or equal to 1.5 times, even more preferably less than or equal to 1 time, particularly preferably less than or equal to 0.7 times, further preferably less than or equal to 0.6 times, further more preferably less than or equal to 0.5 times, further even more preferably less than or equal to 0.2 times, further particularly preferably less than or equal to 0.1 times, and further still even more preferably less than or equal to 0.02 times the mass of methyl mercaptan in the gas in the sealed space. In particular, the gas in the sealed space preferably does not contain dimethyl trisulfide, and most preferably does not contain either dimethyl disulfide or dimethyl trisulfide.

The mass of each of methyl mercaptan, dimethyl disulfide, and dimethyl trisulfide in the gas in the sealed space of the vial (in 19-fold volume of the gas relative to the solution) when the vial is maintained at 40° C. for 30 minutes can be measured by maintaining the vial at 40° C. for 30 minutes, collecting the smell components present in the headspace of the vial with an SPME fiber (PDMS/DVB) for 30 minutes while maintaining the vial at 40° C., and then performing GC/MS analysis.

Return Smell

In the pigment composition according to the present invention, "return smell" of sulfur odor derived from sulfur compounds, which is a major problem of Brassicaceae plant pigments in general, is theoretically highly unlikely to be generated. In addition, even if sulfur odor is generated, the quality of the odor is different from that of common Brassicaceae plant pigments, i.e., the odor is not accompanied by "stuffy odor."

This is because the compounds contained in the pigment composition are those in which sulfur odor components are less likely to be generated even after the compounds undergo, for example, decomposition or synthesis. In other words, this is because the pigment composition has a component composition that renders it less likely to generate sulfur odor components. In particular, dimethyl disulfide and dimethyl trisulfide, which are causative factors of "stuffy odor," are very unlikely to be generated in the pigment composition according to the present invention.

Because of the component composition, the pigment composition according to the present invention has properties in which return smell is theoretically less likely to be generated, even after long-term storage and/or heating. Even if return smell is generated, the odor is not accompanied by stuffy odor. In this regard, the pigment composition according to the present invention is clearly distinct in quality from existing pigment products produced in pursuit of purification and deodorization steps.

For example, even in the case of long-term storage at high temperature (more specifically, even when a pigment-composition-containing aqueous solution containing the pigment composition, 0.2 mass % citric acid, 20 mass % ethanol, and water is prepared so as to have a color value $E^{10\%}_{1cm}$ of 10 and stored at 50° C. for 5 days), the amounts of sulfur compounds generated, which cause sulfur odor, are greatly suppressed. Specifically, the total amount of methyl mercaptan, dimethyl disulfide, and dimethyl trisulfide generated is less than or equal to the reference value described in (B) above, indicating that the total amount is too low to clearly determine that return smell has been generated.

Moreover, even when the pigment composition according to the present invention is stored for a long period of time at high temperature in the same manner as described above, the amounts of dimethyl disulfide and dimethyl trisulfide generated are significantly suppressed, or neither of them is generated. Further, even when the pigment composition according to the present invention is stored for a long period of time at high temperature, the ratio of the total mass of dimethyl disulfide and dimethyl trisulfide to the mass of methyl mercaptan is less than or equal to the reference value described in (D) above, indicating that generation of stuffy odor is hard to perceive.

In contrast, when a solution of common red cabbage pigment is stored for a long period of time at high temperature in the same manner as above and the amounts of sulfur compounds generated are measured, the total amount of methyl mercaptan, dimethyl disulfide, and dimethyl trisulfide, which are sulfur odor components, is notably increased. In particular, the ratio of the total mass of dimethyl disulfide and dimethyl trisulfide to the mass of methyl mercaptan is significantly increased as compared with before long-term storage at high temperature.

As described above, red cabbage pigment stored at high temperature undergoes generation of much larger amounts of sulfur odor components (in particular, stuffy odor components) than the pigment composition according to the present invention. This is because precursors of sulfur compounds contained in red cabbage pigment decompose to produce large amounts of substances causing sulfur odor, resulting in generation of "return smell."

5-Methylthiopentanenitrile

As smell characteristics because of its smell component composition, the pigment composition according to the present invention has a rapeseed-like smell of the same quality as red cabbage pigment in the unrefined stage or the simple purification stage. Specifically, unlike conventional colored radish pigments containing 4MTB-GSL (common wild-type colored radish pigments), the pigment composition according to the present invention has excellent smell characteristics even in the unrefined stage or the simple purification stage.

Specifically, the pigment composition according to the present invention has the following feature:
(C) the gas in the sealed space of the vial contains 5-methylthiopentanenitrile when the vial is maintained at 40° C. for 30 minutes in (B) above.

More specifically, the pigment composition according to the present invention contains 5-methylthiopentanenitrile in the unrefined stage or the simple purification stage. Here, "5-methylthiopentanenitrile" is a smell component that is abundant in red cabbage and that has a weak smell described as a "rapeseed-like smell." This compound is contained in unrefined red cabbage pigment extracted from red cabbage. Because of good smell quality and weak smell intensity, this smell component is not problematic when generally used for, for example, foods and beverages (e.g., used with other flavors etc.).

Although common wild-type colored radish contains 5-methylthiopentanenitrile, the smell of the component is nearly imperceptible because it is masked by a strong odor particular to radish.

In the present invention, whether "the gas in the sealed space of the vial contains 5-methylthiopentanenitrile when the vial is maintained at 40° C. for 30 minutes in (B) above" can be determined by maintaining the vial at 40° C. for 30 minutes, collecting the smell components present in the headspace of the vial while maintaining the vial at 40° C. with an SPME fiber (PDMS/DVB) for 30 minutes, and performing GC/MS analysis.

5-methylthiopentanenitrile is a substance that is not confirmed to be present in plants that do not belong to the family Brassicaceae, such as purple sweet potato. In at least pigment compositions obtained from purple sweet potato, the amount of 5-methylthiopentanenitrile as a smell component is below the detection limit of GC/MS, and its presence is not confirmed.

The pigment composition according to the present invention can be subjected to a purification and/or deodorization step to obtain a pigment composition (or a pigment preparation) that contains a significantly reduced amount of 5-methylthiopentanenitrile, or that is free of 5-methylthiopentanenitrile.

2. Raw Material Radish

Anthocyanin-Pigment-Containing Colored Radish Exhibiting 4MTB-GSL Deficiency

The pigment composition according to the present invention is obtained using a plant other than red cabbage as a raw material. More specifically, the pigment composition according to the present invention is preferably obtained using a specific colored radish as the plant used as a raw material.

The "specific colored radish" that can be used as a raw material in the present invention refers to a radish having both "4MTB-GSL-deficient trait" and "trait of containing an anthocyanin pigment." Hereinafter, a radish having both traits may be referred to as "4MTB-GSL-deficient colored radish" in the present specification.

The finding that the pigment composition according to the present invention has favorable smell characteristics as a pigment composition (i.e., characteristics in which sulfur odor (in particular, stuffy odor) is significantly suppressed and a rapeseed-like smell is emitted) was revealed for the first time by preparing the pigment composition from a raw material, and analyzing and evaluating the composition.

In this regard, it is impossible to determine, only by analyzing and evaluating a colored radish used as a "raw material," that the suitable smell characteristics of the pigment composition according to the present invention are suitable at a level that is the same as or higher than that of red cabbage.

Additionally, in Brassicaceae plants, plants of the genus *Brassica*, to which red cabbage belongs, do not contain 4MTB-GSL.

In this regard, the "4MTB-GSL-deficient colored radish" that can be used as a raw material in the present invention and "red cabbage" have common properties in terms of the glucosinolate components contained therein. As described below, common radish is a 4MTB-GSL-containing plant.

However, "red cabbage pigment" prepared from red cabbage has problematic limited application because return smell is generated by heating or storage. In contrast, in the pigment composition according to the present invention, return smell is significantly suppressed. In particular, generation of return smell of stuffy odor is completely avoided or significantly suppressed.

These findings indicate that depending on the plant species, there is not necessarily a correspondence between the "4MTB-GSL-deficient trait" and "generation of return smell" in Brassicaceae plants, as shown in Table 1.

TABLE 1

| | Presence or absence of 4MTB-GSL | Return smell (stuffy odor) |
| --- | --- | --- |
| Common radish | Contains (presence) | Generated |
| Red cabbage | Lacks (absence) | Generated |
| Colored radish that can be used in the present invention | Lacks (absence) | Not generated |

The use of such a colored radish as an extraction raw material in the production of the pigment composition according to the present invention provides great advantages in terms of pigment quality and production process compared with "red cabbage pigment." The main advantages are as follows.

First, the problems of sulfur odor (in particular, stuffy odor) and the return smell thereof can be ameliorated radically and dramatically. Because of this, the quality of the pigment composition (in particular, the quality of the pigment preparation) is dramatically improved, allowing use in new applications that have been heretofore unavailable.

Second, with the radical amelioration in sulfur odor (in particular, stuffy odor) and the return smell thereof, purification and deodorization steps can be removed or significantly reduced. This enables production efficiency of the pigment composition (in particular, pigment preparation) to be notably improved.

Third, the colored radish used as a raw material is easier to cultivate as a crop than red cabbage, resulting in stable supply of the raw material. Additionally, high production efficiency of the colored radish used as a raw material is also an advantage. Because of these advantages resulting from the raw material, the raw material cost in the pigment production can be expected to be significantly reduced.

4MTB-GSL Deficiency

The anthocyanin pigment composition according to the present invention can be obtained using a colored radish having both the "4MTB-GSL-deficient trait" and the "trait of containing an anthocyanin pigment" as a raw material. As used herein, "4MTB-GSL" (4-methylthio-3-butenyl glucosinolate) is a compound also called glucoraphasatin.

In Brassicaceae plants, 120 or more kinds of glucosinolates having different compound structures have been reported; however, 4MTB-GSL is a compound confirmed to be present only in radish.

"Radish" is a plant species that belongs to Brassicaceae *Raphanus sativus*, and whose enlarged root is used mainly for food. Its sprouts (radish sprouts), baby leaves, and leaves are also used for food.

At the time of filing the present application, a thousand or more cultivar lines, including *R. sativus* var. *longipinnatus*, *R. sativus* var. *sativus*, and *R. sativus* Var. *niger*, were known to exist throughout the world. Almost all of these cultivar lines (except for the below-described cultivar "Daikon Radish Parental Line No. 5" and the "radish lines produced by the present inventors") contain 4MTB-GSL as a main glucosinolate component. As much as 90% or more of the total glucosinolate amount in radish is 4MTB-GSL.

The colored radish that can be used as a raw material in the present invention has the trait of lacking 4MTB-GSL, which is a main glucosinolate component of common wild-type radish, (i.e., 4MTB-GSL deficiency). As used herein, "4MTB-GSL deficiency" refers to a characteristic in which no or almost no 4MTB-GSL is contained.

The content of 4MTB-GSL can be used as a means for determining whether the colored radish that can be used as a raw material in the present invention is deficient in 4MTB-GSL.

More specifically, when the content of 4MTB-GSL in the enlarged root portion (the root and the hypocotyl portion) is 2 μmol/g or less, preferably 1 μmol/g or less, more preferably 0.5 μmol/g or less, and even more preferably 0.1 μmol/g or less on a dry weight basis, it can be determined that the radish is a 4MTB-GSL-deficient radish. The radish most preferably does not contain 4MTB-GSL in the enlarged root portion. When the content is below the detection limit by usual HPLC analysis, the content is at a trace level and is determined to satisfy the above criteria.

Trait of Containing Anthocyanin Pigment

The colored radish used as a raw material of the pigment composition according to the present invention has the trait of containing an anthocyanin pigment, in addition to the 4MTB-GSL-deficient trait described above.

As used herein, "trait of containing an anthocyanin pigment" refers to the trait of containing pelargonidin-type anthocyanin(s) and/or cyanidin-type anthocyanin(s) as main anthocyanin pigment.

The colored radish used as a raw material is preferably a radish having a high content of pelargonidin-type anthocyanin and/or cyanidin-type anthocyanin. More specifically, it is preferable to use a colored radish having, as a raw material, a color value of 0.05 or more, preferably 0.1 or more, and more preferably 0.2 or more. When preparing a pigment composition having a high color value while reducing the burden of the concentration step is desired, the color value as a raw material is 0.5 or more, preferably 1 or more, more preferably 2 or more, and even more preferably 3 or more.

As the colored radish used as a raw material, for example, a radish partially having such a color value may be used, or a portion of the radish having such a color value may be selected and used as a raw material of the pigment composition according to the present invention.

As a raw material used in the present invention, a radish having a high anthocyanin pigment content in the enlarged root portion (in particular, not only the epidermis, but also the entire parenchyma of the root) is particularly suitably used. This is because the enlarged root portion of a radish serves as a suitable raw material in terms of yield ratio and cultivation stability.

Regarding color development characteristics of the pigment composition according to the present invention, the proportions of pelargonidin-type anthocyanin and cyanidin-type anthocyanin can be changed by selecting the type of colored radish used as a raw material. Specifically, because of this, the exhibited hue of the pigment composition can be adjusted in a wide range.

For example, when a colored radish containing a large amount of pelargonidin-type anthocyanin is used as a raw material, a pigment composition exhibiting hues ranging from orange-red to red in an acidic range can be prepared. On the other hand, when a colored radish containing a large amount of cyanidin-type anthocyanin is used as a raw material, a pigment composition exhibiting hues ranging from red-purple to purple in an acidic range can be prepared.

When a radish containing approximately equal amounts of pelargonidin-type anthocyanin and cyanidin-type anthocyanin is used, a pigment exhibiting hues similar to hues ranging from red to red-purple in an acidic range can be prepared.

Other Traits

It is more suitable that the colored radish used as a raw material of the pigment composition according to the present invention has trait(s) that are favorable for the quality of the pigment composition or the production process, as trait(s) other than the above-mentioned traits.

For example, from the viewpoint of yield, the radish preferably has a trait such that its enlarged root portion is thick and long, and such that the parenchyma in the root portion is dense.

When the radish has a trait of excellent growth characteristics, a trait of excellent environmental tolerance, a trait of excellent disease resistance, etc., the production of the raw material as a crop becomes easy, resulting in reduced raw material supply costs. It is thus suitable.

Means for Producing Colored Radish Having 4MTB-GSL-Deficient Trait as a Raw Material The colored radish that can be used as a raw material in the present invention can be produced using a "radish having a 4MTB-GSL-deficient trait" and a "colored radish having a trait of containing an anthocyanin pigment" according to a usual breeding technique.

More specifically, the "radish having a 4MTB-GSL-deficient trait" can be crossed with the "colored radish having a trait of containing an anthocyanin pigment" to obtain a radish having both traits.

A colored radish having a desired excellent trait can be obtained by repeating, for example, crossing, selfing, and selection. Examples of excellent traits include a trait in which 4MTB-GSL deficiency is particularly enhanced, a trait in which the anthocyanin composition exhibits a desired hue, a trait in which the anthocyanin pigment content is particularly high (a trait in which the color value as a raw material is high), a trait in which the enlarged root portion has suitable properties, and the like.

In particular, regarding quantitative traits (such as the anthocyanin pigment content), a colored radish in which a desired trait is further enhanced can be obtained by performing, for example, (i) backcross and selection (a method in which backcrossing with a donor parent of an excellent trait is performed, and an excellent radish is selected from the backcross population), (ii) mass selection (a method in which in a population of individual radishes with a desired trait, crossing is freely performed to obtain an improved excellent population), and (iii) selfing operation and selection. For example, a radish in which the anthocyanin pigment content is increased can be obtained by performing steps (i) to (iii).

In addition, a line or a cultivar can be produced by obtaining a population having both of the above traits genetically fixed therein.

Donor Parent of 4MTB-GSL-Deficient Trait

The "radish having a 4MTB-GSL-deficient trait" used as a crossing parent may be any radish that shows 4MTB-GSL deficiency as a phenotype. It is preferable to use a radish with a high degree of 4MTB-GSL deficiency. 4MTB-GSL deficiency can be determined by measuring the glucosinolate composition (4MTB-GSL content) in the enlarged root portion, as described above.

Examples of cultivar lines having this trait include those having a 4MTB-GSL-deficient trait due to the same or substantially the same genetic factor as that of "Daikon Radish Parental Line No. 5."

Examples of cultivar lines having "the same genetic factor" include (a) cultivar "Daikon Radish Parental Line No. 5" itself. Examples also include (b) cultivar lines that are derived from "Daikon Radish Parental Line No. 5," and that have a 4MTB-GSL-deficient trait. Examples further include (c) cultivar lines that are not derived from "Daikon Radish Parental Line No. 5," but that have the same genotype as the genotype of the 4MTB-GSL-deficient trait of "Daikon Radish Parental Line No. 5," and that have a 4MTB-GSL-deficient trait.

Examples of cultivar lines having "substantially the same genetic factor" include the cultivar lines (b) and (c) described above that have small numbers of mutations in a gene responsible for the genetic factor of the trait (for example, substitution(s), insertion(s), addition(s), deletion(s), and/or the like in site(s) that are not greater than 5%, preferably not greater than 1%, and more preferably not greater than 0.1% of the base sequence of the gene); and that maintain the function of the 4MTB-GSL-deficient trait.

The major feature of cultivar "Daikon Radish Parental Line No. 5" is the glucosinolate composition, i.e., the feature that the cultivar has 4MTB-GSL deficiency as a phenotype.

The 4MTB-GSL-deficient trait of the cultivar is a recessive trait controlled by a single genetic factor (Ishida et al., 2011, Breeding Research, Vol. 13, extra issue No. 1, p. 47). Therefore, when the 4MTB-GSL deficiency of the cultivar is introduced into a colored radish, it is necessary to obtain a colored radish into which the trait is introduced such that the locus is homozygous.

Since the cultivar is one with a common color in which almost no anthocyanin pigment is accumulated and whose enlarged root portion is "white," an anthocyanin pigment cannot be extracted only by using this radish cultivar as a raw material.

Donor Parent of Trait of Containing Anthocyanin Pigment

Meanwhile, the "colored radish having a trait of containing an anthocyanin pigment" used as a crossing parent may be any radish that has the trait of containing an anthocyanin pigment, including radishes called red radish, purple radish, or the like.

"Red radish" is a common name that refers to a radish in which the entire plant (especially the root portion) exhibits a red hue or a hue close to red. Red radish is rich in pelargonidin-type anthocyanins. "Purple radish" is a common name that refers to a radish in which the entire plant (especially, the root portion) exhibits a purple hue or a hue close to purple. Purple radish is rich in cyanidin-type anthocyanins.

As a donor parent of this trait, it is preferable to use a radish having a high anthocyanin pigment content. It is particularly preferable to use a radish whose enlarged root portion (in particular, not only the epidermis, but also the entire parenchyma of the root) has a high anthocyanin pigment content. This is because the enlarged root portion of radish serves as a suitable raw material in terms of yield and cultivation stability.

A radish exhibiting a desired hue depending on, for example, the molecular species of pelargonidin-type anthocyanins and/or cyanidin-type anthocyanins, and the content of the each anthocyanin molecules can be used as the donor parent of this trait.

Examples of colored radish cultivar lines include radishes (R. sativus var. longipinnatus) having hues such as orange-red, vermillion, red, purplish red, red-purple, reddish purple, and purple. Specific examples of such radish cultivar lines include "Benikururi," "Momiji stick," "Benigesho," "Karaine aka," "Benikanmi," "Benishigure," "Lady salad," "Benimasari," "Koitten," "Inuidani," "Kurenai sobutori," "Murasaki sobutori," "Shizumurasaki," "Ajiichiban murasaki," "Koshin," "Pekin koshin," "Tenan koshin," "Choan aomarukoshin," "Koga benimaru" "Akane," "Akakubi meyama sangatsu daikon," "Hilds blauer," "Milano," and the like.

Examples also include R. sativus var. sativus having, for example, pink, red, or purple color or tone. Examples of cultivar lines of such R. sativus var. sativus include "Pink Beauty," "Puteruma 2-go," "Red chime," "Linda red," "Scarlet globe," "Hohobenimaru," "Akachan," "Sparkler III," "Jolly," "Benimusume," "Comet," "Shuttlecock," "Isabel," "Sparkler II," "Sakuranbo," "Cherry mate," "Birdland," "Red sun," "Mascot," "Konbi," "Kohaku," "Nelson," "French Breakfast," "Vienna," "Sparkler," "French Breakfast III," "Ribera," "Purple Star," "Amethyst," and the like.

Radishes obtained from crossing between these cultivar lines can also be used as donor parents of this trait. In addition, cultivar lines that are derived from these cultivar lines and that have a trait of containing an anthocyanin pigment can also be used as donor parents of this trait. Furthermore, cultivar lines other than those described above can be used as donor parents of this trait, as long as they are colored radish having a trait of containing an anthocyanin pigment.

Donor Parents for Other Traits

In the production method, it is desirable that the donor parent of the 4MTB-GSL-deficient trait and/or the donor parent of the trait of containing an anthocyanin pigment also have suitable desired trait(s) other than these traits.

When it is desired to obtain a raw material radish further having a desired trait in addition to these traits, a radish having the desired trait (that is not necessarily required to have the trait of containing an anthocyanin pigment or the 4MTB-GSL-deficient trait) can be separately used as a third donor parent to perform crossing and selection, thereby obtaining a radish (and a line) into which the desired trait, in addition to the two traits described above, is introduced.

Suitable desired traits include all traits that are favorable for the quality of the pigment composition and the production process. Examples include traits that improve the quality of the enlarged root portion (e.g., the size of the enlarged root portion, the shape of the enlarged root portion, and the density of the parenchyma in the enlarged root portion), traits related to environmental tolerance (e.g., cold tolerance and heat tolerance), traits related to disease resistance, traits related to growth (e.g., earliness of the cultivation period and plant hormone synthesis system), traits related to reproduction (e.g., flowering control, self-incompatibility, and cytoplasmic male sterility), and the like.

Extraction and Juice-Squeezing Steps

The pigment composition according to the present invention can be obtained by extraction from, or squeezing juice from, the 4MTB-GSL-deficient colored radish raw material described above. The portion of the plant used for extraction or juice-squeezing may be any portion that contains an anthocyanin pigment. It may be the entire plant, or a portion of the plant.

For example, any of roots (including lateral roots and immature roots), hypocotyls, leaves, rachises, stems, flower buds, flowers, seeds, germinated sprouts, and the like can be used. In consideration of the yield of the raw material crop and pigment yield efficiency, it is preferable to use an enlarged root portion including a root and a hypocotyl portion. A mature and developed enlarged root portion is particularly suitable.

Extraction

When an operation of extraction from the raw material plant is performed, the raw material can be used as is for solvent extraction, regardless of the shape of the raw material. To increase the surface area for improving extraction efficiency, it is suitable that the raw material is processed (e.g., crushed or the like). As used herein, "crushed or the like" is an action that encompasses, for example, crushing, pulverization, milling, grinding, and powderization. In addition, "crushed or the like" is an action that also encompasses, for example, chopping into, cutting into, slicing into, and dicing into, small pieces of several millimeters to several centimeters. Dried products obtained by drying these pieces can also be used.

The extraction solvent may be any solvent that can be used for extraction of anthocyanin pigments. Preferable examples include water, hydrous alcohols, alcohols, and the like.

Examples of the type of alcohol include $C_1$-$C_4$ lower alcohols. Specific examples include methanol, ethanol, propanol, isopropyl alcohol, butanol, and the like. Ethanol is preferable.

The solvent is particularly preferably water or a hydrous alcohol. It is suitable that the hydrous alcohol has an alcohol content of 50% (v/v) or less, and preferably 40% (v/v) or less. The lower limit of the alcohol content is not particularly limited, and is, for example, 1% (v/v).

The amount of the solvent relative to the raw material is not particularly limited, and is, for example, 0.1 to 1000 parts by mass per part by mass of the raw material. In particular, the solvent is preferably used in an amount of 0.5 to 100 parts by mass, and more preferably 1 to 50 parts by mass, per part by mass of the raw material.

The extraction solvent is preferably an acidic solution. More specifically, it is suitable that the solvent is an acidic solution adjusted to a pH of 1 to 5, preferably a pH of 1 to 4, and more preferably a pH of 1 to 3.

As a means for adjusting the extraction solvent to be acidic, for example, an inorganic acid and/or an organic acid is added. Examples of inorganic acids include hydrochloric acid, sulfuric acid, nitric acid, phosphoric acid, and the like.

Examples of organic acids include citric acid, acetic acid, malic acid, lactic acid, and the like.

The amount of the inorganic acid and/or organic acid added to the extraction solvent is not particularly limited, and is preferably suitably adjusted within the range of about 0.01 to 10 mass %, preferably about 0.1 to 7.5 mass %, and more preferably about 0.5 to 5 mass %, relative to the extraction solvent.

The extraction operation is not particularly limited, and may be performed according to a usual method. The extraction operation may be performed by immersion or being left to stand. For example, stirring, suspension, shaking, vibration treatment, ultrasonic treatment, or the like can be performed to improve extraction efficiency.

The temperature conditions during extraction are not particularly limited. Extraction is performed at, for example, 100° C. or less, preferably 10 to 70° C., and more preferably 10 to 40° C.

The extraction time is not particularly limited, and is, for example, 1 minute to 72 hours, preferably 10 minutes to 48 hours, and more preferably 30 minutes to 24 hours.

Juice-Squeezing

In the present invention, the desired pigment composition can also be obtained by subjecting the raw material plant to a juice-squeezing operation.

When a juice-squeezing operation is performed, the raw material can be used as is; in view of squeezing efficiency, it is preferable to use a raw material that has been crushed or the like. As used herein, "crushed or the like" is an action that encompasses, for example, crushing, pulverization, milling, and grinding. In addition, "crushed or the like" is an action that also encompasses, for example, chopping into, cutting into, slicing into, and dicing into, small pieces of several millimeters to several centimeters.

Examples of the juice-squeezing operation include, but are not particularly limited to, a method in which juice is squeezed from a plant by applying pressure to the plant by means of, for example, pressing, after which the juice is collected.

Purification Treatment and Deodorization Treatment

An extract or squeezed juice obtained by the operation described above is an embodiment of the anthocyanin pigment composition according to the present invention.

In addition, the extract or squeezed juice can, if necessary, undergo solid-liquid separation (such as filtration, suction filtration, coprecipitation, or centrifugation) to remove solids, insoluble matter, etc. When filtration is performed, a filter aid (such as diatomaceous earth or cellulose) is also suitable for use.

Further, in the present invention, the obtained extract or squeezed juice can, if necessary, be subjected to treatment such as purification and/or deodorization depending on the intended use to obtain a pigment composition of the desired quality and in the desired form.

The purification treatment and/or deodorization treatment can be performed using a usual technique.

For example, the purification treatment and/or deodorization treatment can be performed by adsorption treatment using silica gel, porous ceramic, a styrene or aromatic synthetic resin, or the like. The purification treatment and/or deodorization treatment can also be performed by ion-exchange treatment using a cationic resin or an anionic resin. The purification treatment and/or deodorization treatment can also be performed by membrane separation treatment using a filter membrane, an ultrafiltration membrane, a reverse osmosis membrane, an electrodialysis membrane, a functional polymer membrane, or the like.

Depending on the intended use, enzyme treatment using, for example, protease, microbial treatment, or the like can be performed as the purification treatment and/or deodorization treatment.

Subjecting the pigment composition according to the present invention to the purification treatment or deodorization treatment only a small number of times (for example, about once or twice) allows the composition to be almost or completely odorless.

Because of this, the pigment composition can be used without being limited by odor, even in applications where conventional red cabbage pigment has been difficult to use; therefore, the pigment composition has an advantage in that the composition can be used in any application.

The extract or squeezed juice obtained by the step described above or the solution after purification treatment and/or deodorization treatment can be subjected to an operation such as dilution, concentration, drying, sterilization, filtration, or the like depending on the intended purpose to obtain a pigment composition of the desired quality and in the desired form. The operation such as dilution, concentration, drying, sterilization, or filtration can be performed according to a usual method.

The above-described types of purification treatment and/or deodorization treatment can be used alone, or in a combination of two or more.

Needless to say, a pigment composition obtained by subjecting the pigment composition of the present invention to such purification treatment and/or deodorization treatment is also included in the pigment composition of the present invention.

3. Forms of Pigment Composition and Pigment Preparation, and their Applications

The pigment composition according to the present invention can also be used as a pigment preparation.

The form of the pigment composition (or pigment preparation) according to the present invention is not particularly limited, and is in the form of, for example, a liquid, paste, gel, semi-solid, solid, or powder.

The anthocyanin pigment content in the pigment composition (or pigment preparation) is not particularly limited, and is, for example, preferably 1 to 90 mass %, more preferably 5 to 75 mass %, and even more preferably 10 to 60 mass %.

When the pigment composition is used for coloring applications (for example, when the pigment composition is used as a pigment preparation), it is suitable that the color value $E^{10\%}_{1cm}$ of the pigment composition (or pigment preparation) is 20 or more, preferably 30 or more, and more preferably 40 or more. The upper limit of the color value of the pigment composition (or pigment preparation) is not particularly limited, and is, for example, 800.

Two or more types of the pigment composition (or pigment preparation) having different hues can be mixed to obtain a pigment composition (or pigment preparation) having a desired hue.

For example, a pelargonidin-type-anthocyanin-rich pigment composition (or pigment preparation) and a cyanidin-type-anthocyanin-rich pigment composition (or pigment preparation) can be mixed at a desired ratio to prepare a pigment composition (or pigment preparation) exhibiting a desired hue ranging from orange to red to purple in an acidic range.

The pigment composition according to the present invention can also be mixed with a colorant prepared from a raw material other than that of the present invention (for example, a pigment preparation with a color such as yellow, green, or blue) to obtain a desired hue.

The pigment composition (or pigment preparation) according to the present invention can be used in applications as a coloring agent in which conventional red cabbage pigment is used. From the viewpoint of odor and color, the pigment composition (or pigment preparation) according to the present invention can also be used in applications in which conventional red cabbage pigment cannot be used. The pigment composition (or pigment preparation) according to the present invention can thus be used in a wide variety of applications.

More specifically, the pigment composition (or pigment preparation) according to the present invention can suitably be used as a natural coloring agent used in products, such as foods, beverages, quasi-drugs, pharmaceutical products, fragrances, cosmetics, sanitary commodities, and feed.

The proportion of the pigment composition (or pigment preparation) according to the present invention in such a product can suitably be adjusted according to the type or purpose of product. For example, the pigment composition can be used in an amount such that the content of the pigment composition in a product is 0.001 to 1 mass %, preferably 0.005 to 0.5 mass %, more preferably 0.01 to 0.2 mass %, and even more preferably 0.02 to 0.1 mass %, in terms of a color value of 80.

As used herein, "in terms of a color value of 80" means that the amount of the pigment composition (pigment preparation) of the present invention is converted to a value based on a color value of 80. The value based on a color value of 80 can be calculated by multiplying the amount of the pigment composition (pigment preparation) by the color value ratio. For example, when a pigment composition having a color value of 160 is used in an amount of 0.5 mass %, the amount of the composition added, i.e., 0.5 mass % is multiplied by a color value ratio of 2 (160/80), thereby obtaining 1 mass % as the value based on a color value of 80.

The present invention also provides a method for producing the anthocyanin pigment composition of the present invention.

An embodiment of the production method comprises extracting an anthocyanin pigment from an anthocyanin-pigment-containing colored radish exhibiting 4-methylthio-3-butenyl glucosinolate deficiency.

Another embodiment of the production method comprises squeezing juice from an anthocyanin-pigment-containing colored radish exhibiting 4-methylthio-3-butenyl glucosinolate deficiency.

Based on the foregoing description of the anthocyanin pigment composition etc. of the present invention, those skilled in the art can understand the method for producing an anthocyanin pigment composition of the present invention.

EXAMPLES

The present invention is described in more detail below with reference to Examples; however, it is not limited to these Examples.

Example 1

Production of Anthocyanin Pigment Compositions (Pigment Preparations)

Anthocyanin pigment compositions (pigment preparations) were prepared using colored radishes exhibiting 4MTB-GSL deficiency as raw materials.

(1) Production of Colored Radishes Exhibiting 4MTB-GSL Deficiency

Radish cultivar "Daikon Radish Parental Line No. 5," which has a 4MTB-GSL deficient trait, was crossed with colored radish cultivar "Tenan koshin," which has a trait of containing an anthocyanin pigment. A radish that exhibited 4MTB-GSL deficiency and whose enlarged root portion was purple was then selected from the $F_2$ population.

To further increase the color value, the selected $F_2$ radish was crossed with a red inbred line derived from Chinese watermelon radish, and a radish with intense purple color having a high color value as a raw material and exhibiting 4MTB-GSL deficiency was selected from the progeny to produce a line (FIG. 1, reference numeral 1).

In the same manner as above, a radish that exhibited 4MTB-GSL deficiency and whose enlarged root portion was red was selected from the $F_2$ population, and crossed with a red inbred line derived from Chinese watermelon radish. A radish with intense red color having a high color value as a raw material and exhibiting 4MTB-GSL deficiency was then selected from the progeny to produce a line (FIG. 1, reference numeral 2).

(2) Preparation of Anthocyanin Pigment Compositions (Pigment Preparations)

Figure 2:
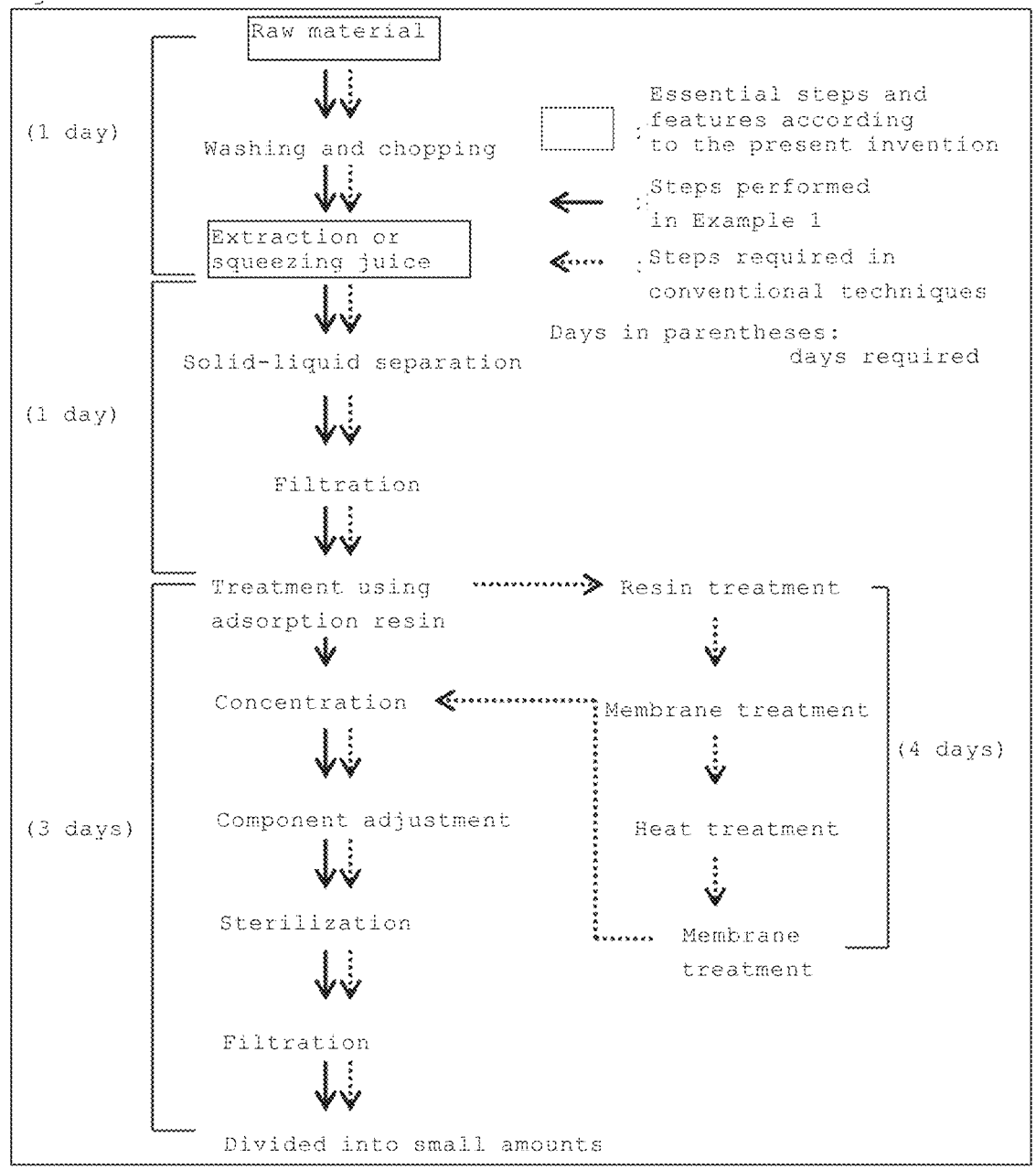
FIG. 2 is a flow chart of the process for producing an anthocyanin pigment preparation from a raw material in the production of the pigment preparations in Example 1.

Pigment compositions (pigment preparations) were individually prepared using the enlarged root portions of the 4MTB-GSL-deficient colored radishes of the produced lines described above and common wild-type colored radishes (comparative raw materials). FIG. 2 shows a process flow in the preparation example.

Each enlarged root portion was individually cut into squares of roughly 3 mm with a food processor, and extraction was performed using 0.5% aqueous sulfuric acid in an amount twice the weight of the raw material. For the extraction operation, stirring treatment was performed at room temperature for 1 hour, followed by being left to stand at room temperature for 12 hours. After being left to stand, solid-liquid separation was performed using a 20 mesh sieve to collect an extract.

The residue, i.e., the solids, were subjected to re-extraction by stirring treatment at room temperature for 1 hour using 0.5% aqueous sulfuric acid in an amount twice the weight of the raw materials, and solid-liquid separation was performed to obtain a re-extract.

The obtained extract and re-extract were mixed (note that in the case of the comparative raw materials, i.e., the wild-type colored radishes, only the extract was used), and diatomaceous earth, which is a filter aid, was added in an amount of 1 part by mass based on the liquid amount, and mixed. The mixture was subjected to suction filtration using filter paper (No. 2 filter produced by Toyo Roshi Kaisha, Ltd.; φ 150 mm) on which a layer of 20 g of the diatomaceous earth was formed beforehand, thereby collecting a filtrate.

The obtained filtrate was passed through a column packed with a synthetic adsorption resin for adsorption. After adsorption, the column was washed with deionized water in an amount three times the volume of the adsorption resin. Pigment components were desorbed from the adsorption resin using 60% (v/v) aqueous ethanol containing 0.3% (w/w) citric acid, in an amount twice the volume of the adsorption resin.

The solution collected from the column was concentrated under reduced pressure to prepare a concentrated solution such that the color value $E^{10\%}_{1cm}$, was about 110, the citric acid concentration was 6% (w/w), and the ethanol concentration was 20% (w/w). The concentrated solution was sterilized by heat at 60° C. for 1 minute, passed through a 150 mesh sieve, and divided into small amounts. Anthocyanin pigment compositions (pigment preparations) (samples 1 to 4) were thereby obtained.

The color value $E^{10\%}_{1cm}$ was calculated using a citrate buffer (pH: 3.0) as a solvent according to the method described in Japan's Specifications and Standards for Food Additives, 8th ed. (Ministry of Health, Labour and Welfare, Japan).

(3) Production Data

The production amount (liquid weight) of each of the prepared pigment preparations (samples) was measured. The color value $E^{10\%}_{1cm}$ was calculated in the same manner as described above. Table 2 shows the results.

The results revealed that even when the colored radishes exhibiting 4MTB-GSL deficiency were used as raw materials, pigment preparations were produced in high yields similar to those of the common wild-type colored radishes.

In addition, measurement of the maximum absorption wavelength of each pigment preparation (sample) at a pH of 3.0 showed that the maximum absorption wavelengths of the pigment preparations obtained using the purple radishes as raw materials were near 530 nm, and that the maximum absorption wavelengths of the pigment preparations obtained using the red radishes as raw materials were near 516 nm.

TABLE 2

| | Raw material | | Pigment preparation ($E^{10\%}_{1cm}$ value = adjusted to about 110) | | |
|---|---|---|---|---|---|
| | Type | Total weight (g) | Production amount (g) | Color value ($E^{10\%}_{1cm}$ value) | λmax (nm) |
| Sample 1 | 4MT3-GSL deficient purple radish | 7664.5 | 92.2 | 110.47 | 529 |
| Sample 2 | 4MT3-GSL deficient red radish | 3318.5 | 75.1 | 110.39 | 515 |
| Sample 3 | Wild-type purple radish (comparative raw material) | 7845.7 | 64.0 | 108.00 | 531 |
| Sample 4 | wild-type red radish (comparative raw material) | 9263.5 | 102.0 | 106.01 | 517 |

Example 2

Evaluation of Color Development Characteristics of Pigment Preparations (Color Change Depending on pH)

Color changes depending on the pH in each of the pigment preparations of the 4MTB-GSL-deficient colored radishes prepared in Example 1 were analyzed in detail and compared with those of red cabbage pigment.

(1) Hunter Lab Color System

For each pigment preparation, test liquids having different pHs were prepared. More specifically, each pigment preparation was individually added to and dissolved in the buffers of various pHs shown in Tables 3 to 5 below (pH 2.0 to 8.0: McIlvaine buffer, and pH 9.0: buffer adjusted to a pH of 9.0 by adding sodium hydroxide to McIlvaine buffer) such that the amount of the pigment preparation was 0.05% (w/w) in terms of a color value $E^{10\%}_{1cm}$ of 60, thereby preparing test liquids. As a control, a commercially available red cabbage pigment preparation (produced by San-Ei Gen F.F.I., Inc.) was used.

Colorimetry was performed for each of the prepared test liquids by measuring transmitted light at measurement wavelengths of 380 to 780 nm using a spectrophotometer (V-560 produced by JASCO Corporation; optical path length of measurement cell: 1 cm) to measure the tristimulus values (L, a, and b values) of the Hunter Lab color system.

The Hunter Lab color system (Lab system) is a color system represented using a color solid composed of a- and b-axis rectangular coordinates, which indicate chromaticity, and an L-axis perpendicular to the a- and b-axes. The "L value" indicates lightness, with L=100 being white and L=0 being black. The "a value" indicates red/green hue. A larger positive "a value" denotes a redder color, whereas a larger negative "a value" denotes a greener color. The "b value" indicates yellow/blue hue. A larger positive "b value" denotes a yellower color, whereas a larger negative "b value" denotes a bluer color.

Tables 3 to 5 show the measured values of the Hunter Lab color system.

TABLE 3

| Red cabbage pigment (control sample: commercially available product) | L value | a value | b value |
| --- | --- | --- | --- |
| pH 2.0 | 79.28 | 43.10 | −7.31 |
| pH 3.0 | 84.80 | 29.76 | −7.94 |
| pH 4.0 | 88.13 | 15.67 | −5.92 |
| pH 5.0 | 92.46 | 8.77 | −6.47 |
| pH 6.0 | 92.07 | 7.56 | −7.12 |
| pH 7.0 | 84.91 | 6.19 | −15.02 |
| pH 8.0 | 70.15 | −3.38 | −33.85 |
| pH 9.0 | 69.40 | −10.48 | −29.37 |

TABLE 4

| 4MTB-GSL-deficient purple radish pigment (sample 1: product of Example) | L value | a value | b value |
| --- | --- | --- | --- |
| pH 2.0 | 80.98 | 41.24 | −7.62 |
| pH 3.0 | 85.67 | 29.82 | −8.08 |
| pH 4.0 | 91.27 | 16.20 | −6.68 |
| pH 5.0 | 95.30 | 6.63 | −4.73 |
| pH 6.0 | 96.07 | 4.51 | −4.52 |
| pH 7.0 | 91.48 | 4.92 | −9.35 |
| pH 8.0 | 72.85 | −0.38 | −33.53 |
| pH 9.0 | 67.21 | −4.68 | −41.00 |

TABLE 5

| 4MTB-GSL-deficient red radish pigment (sample 2: product of Example) | L value | a value | b value |
| --- | --- | --- | --- |
| pH 2.0 | 85.97 | 29.25 | 5.62 |
| pH 3.0 | 88.67 | 23.73 | 1.43 |
| pH 4.0 | 92.85 | 14.41 | −1.68 |
| pH 5.0 | 96.20 | 6.65 | −2.70 |
| pH 6.0 | 96.68 | 5.09 | −2.93 |
| pH 7.0 | 92.11 | 9.06 | −7.71 |
| pH 8.0 | 72.88 | 17.80 | −30.75 |
| pH 9.0 | 68.95 | 14.71 | −35.37 |

(2) Evaluation of Color

Based on the values described above, lightness, chroma, and hue were evaluated. "Lightness" was evaluated using an L value (Table 6). "Chroma" was evaluated using a chroma value calculated according to the following (Equation 2) (Table 7). The chroma value represents the distance from the origin in the Hunter Lab color system. The larger the chroma value, the more vivid the color.

Figure 3:
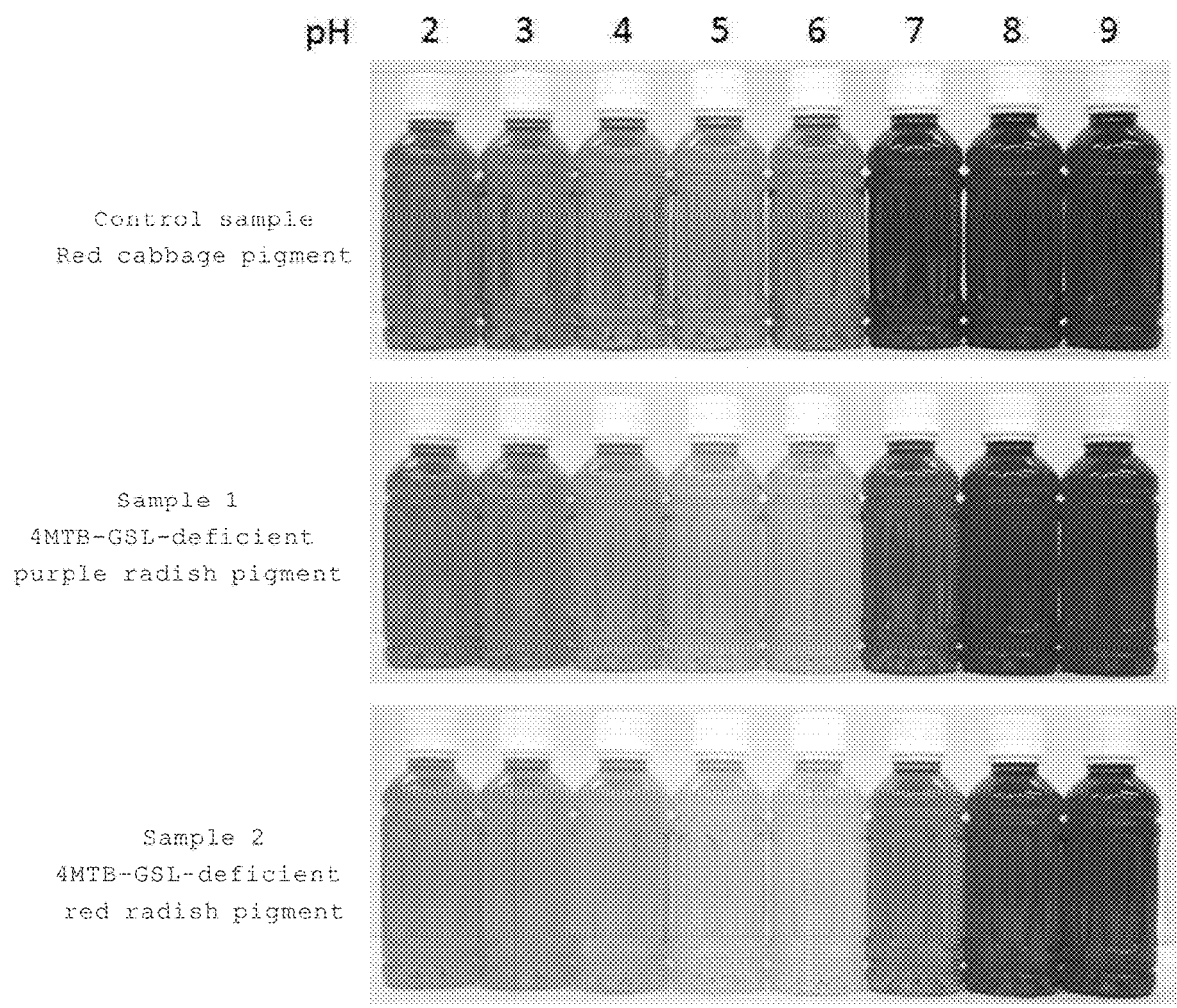
FIG. 3 shows photographs indicating changes in the color of the colored radish pigments and red cabbage pigment (control sample) with changes in the pH in the color analysis of the pigment preparations in Example 2.

"Hue" was evaluated by calculating a hue value (Table 8). The hue value consists of letters and a numerical value that indicate hue, and is obtained by converting an angle formed by a straight line connecting the origin to a plot ("a value" and "b value") on the a- and b-axis rectangular coordinates in the Hunter Lab color system, into a hue notation in a Munsell hue circle. Table 9 shows JIS color names corresponding to the hue values. FIG. 3 shows the photographs of the prepared test liquids filled in PET bottles.

Figure 4:
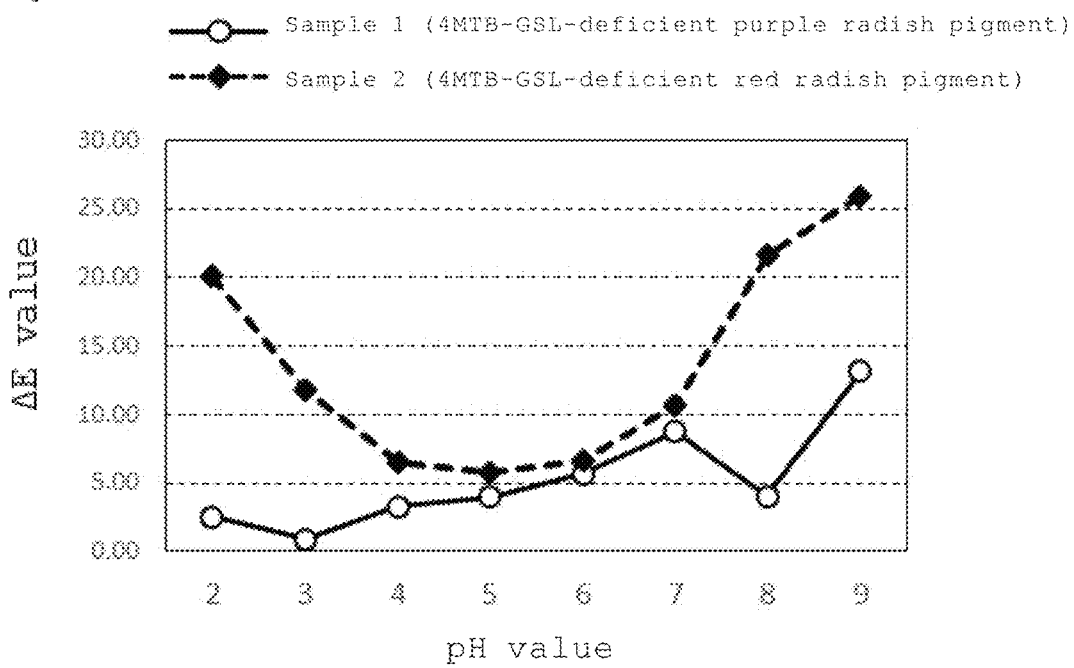
FIG. 4 is a graph showing changes in the ΔE value (color difference) between each colored radish pigment and the red cabbage pigment (control sample) with changes in the pH in the color analysis of the pigment preparations in Example 2.

In addition, each sample (4MTB-GSL-deficient colored radish pigment preparation) was compared with the red cabbage pigment (control sample), and the color difference between the two (distance between two colors), which is indicated by a ΔE value, was calculated using the following (Equation 3) (Table 10 and FIG. 4).

$$\text{CHROMA} = \sqrt{a^2 + b^2} \quad \text{(Equation 2)}$$

$$\Delta E = \sqrt{(L_1 - L_2)^2 + (a_1 - a_2)^2 + (b_1 - b_2)^2} \quad \text{(Equation 3)}$$

Based on the obtained analysis results, the color of each pigment preparation was evaluated comprehensively.

The results showed that the "4MTB-GSL-deficient purple radish pigment preparation" (sample 1) exhibited color similar to that of the red cabbage pigment (control sample) in all of hue, chroma, and lightness in a wide pH range of 2.0 to 8.0 (acidic to weakly alkaline).

In particular, the color difference (ΔE) indicated that the "4MTB-GSL-deficient purple radish pigment preparation" exhibited color very close to that of the red cabbage pigment (control sample) at a pH of 2.0 to 5.0 (in particular, a pH of 2.0 to 4.0), which is an acidic range.

On the other hand, as is clear from the hue and chroma values, the "4MTB-GSL-deficient red radish pigment preparation" (sample 2) exhibited color that was significant different from that of the red cabbage pigment (control sample).

In particular, the color difference (ΔE) indicated that the "4MTB-GSL-deficient red radish pigment preparation" exhibited color that was significantly different from that of the red cabbage pigment (control sample) at a pH of 2.0 to 4.0 (in particular, a pH of 2.0 to 3.0), which is an acidic range, and at a pH of 6.0 to 9.0 (in particular, a pH of 7.0 to 9.0), which is an alkaline range.

TABLE 6

| Lightness (L value) | Control sample Red cabbage pigment | Sample 1 4MTB-GSL-deficient purple radish pigment | Sample 2 4MTB-GSL-deficient red radish pigment |
| --- | --- | --- | --- |
| pH 2.0 | 79.28 | 80.98 | 85.97 |
| pH 3.0 | 84.80 | 85.67 | 88.67 |
| pH 4.0 | 88.13 | 91.27 | 92.85 |
| pH 5.0 | 92.46 | 95.30 | 96.20 |
| pH 6.0 | 92.07 | 96.07 | 96.68 |
| pH 7.0 | 84.91 | 91.48 | 92.11 |
| pH 8.0 | 70.15 | 72.85 | 72.88 |
| pH 9.0 | 69.40 | 67.21 | 68.95 |

TABLE 7

| Chroma (chroma value) | Control sample Red cabbage pigment | Sample 1 AMTR-GSL-deficient purple radish pigment | Sample 2 4MTB-GSL-deficient red radish pigment |
| --- | --- | --- | --- |
| pH 2.0 | 43.72 | 41.94 | 29.79 |
| pH 3.0 | 30.80 | 30.90 | 23.77 |
| pH 4.0 | 16.75 | 17.52 | 14.51 |
| pH 5.0 | 10.90 | 8.14 | 7.18 |
| pH 6.0 | 10.38 | 6.39 | 5.87 |
| pH 7.0 | 16.25 | 10.57 | 11.90 |
| pH 8.0 | 34.02 | 33.53 | 35.53 |
| pH 9.0 | 31.18 | 41.27 | 38.31 |

TABLE 8

| Hue (hue value) | Control sample Red cabbage pigment | Sample 1 4MTB-GSL-deficient purple radish pigment | Sample 2 4MTB-GSL-deficient red radish pigment |
| --- | --- | --- | --- |
| pH 2.0 | 7.3RP | 7.1RP | 3.0R |
| pH 3.0 | 5.9RP | 5.8RP | 1.0R |
| pH 4.0 | 4.3RP | 3.8RP | 8.2RP |
| pH 5.0 | 9.9P | 0.1RP | 3.9RP |
| pH 6.0 | 8.0P | 7.5P | 1.7RP |
| pH 7.0 | 1.2P | 2.7P | 8.8P |
| pH 8.0 | 3.4PB | 4.8PB | 3.4P |
| pH 9.0 | 9.5B | 3.2PB | 1.3P |

TABLE 9

| Hue color (JIS color-name) | Control sample Red cabbage pigment | Sample 1 4MTB-GSL-deficient purple radish pigment | Sample 2 4MTB-GSL-deficient red radish pigment |
| --- | --- | --- | --- |
| pH 2.0 | Purplish red to red-purple | Purplish red to red-purple | Red to purplish red |
| pH 3.0 | Purplish red to red-purple | Purplish red to red-purple | Red to purplish red |
| pH 4.0 | Red-purple to reddish purple | Red-purple to reddish purple | Purplish red to red-purple |
| pH 5.0 | Reddish purple | Reddish purple | Red-purple to reddish purple |
| pH 6.0 | Reddish purple to purple | Reddish purple to purple | Red-purple to reddish purple |
| pH 7.0 | Purple to blue-purple | Purple to blue-purple | Reddish purple to purple |
| pH 8.0 | Purplish blue to blue | Purplish blue | Purple to blue-purple |
| pH 9.0 | Blue | Purplish blue to blue | Purple to blue-purple |

TABLE 10

| Color difference (ΔE value) | Control sample Red cabbage pigment | Sample 1 4MTB-GSL-deficient purple radish pigment | Sample 2 4MTB-GSL-deficient red radish pigment |
| --- | --- | --- | --- |
| pH 2.0 | — | 2.54 | 20.09 |
| pH 3.0 | — | 0.88 | 11.80 |
| pH 4.0 | — | 3.27 | 6.47 |
| pH 5.0 | — | 3.96 | 5.72 |
| pH 6.0 | — | 5.66 | 6.70 |
| pH 7.0 | — | 8.77 | 10.65 |
| pH 8.0 | — | 4.05 | 21.58 |
| pH 9.0 | — | 13.18 | 25.90 |

Example 3

Evaluation of Color Development Characteristics of Pigment Preparations (Comparison with Other Anthocyanin Pigments)

The colors of the pigment preparations of the 4MTB-GSL-deficient colored radishes prepared in Example 1 were compared with those of anthocyanin pigments derived from other natural raw materials.

(1) Hunter Lab Color System

Test liquids of the pigment preparations having a pH of 3.0 were prepared. More specifically, each pigment preparation was individually added to and dissolved in a citrate buffer (pH: 3.0) such that the amount of the pigment preparation was 0.03% (w/w) in terms of a color value $E^{10\%}_{1cm}$ of 80, thereby preparing test liquids. As a control sample and comparative samples, anthocyanin pigments produced by San-Ei Gen F.F.I., Inc. were used.

Colorimetry was performed for each of the prepared test liquids by measuring transmitted light at measurement wavelengths of 380 to 780 nm using a spectrophotometer (V-560 produced by JASCO Corporation; optical path length of measurement cell: 1 cm) to measure L, a, and b values. Table 11 shows the measured values of the Lab color system.

TABLE 11

| Sample | Pigment name | L value | a value | b value |
| --- | --- | --- | --- | --- |
| Control sample (commercially available product) | Red cabbage pigment | 87.48 | 25.57 | −7.29 |
| Sample 1 (product of Example) | 4MTBG-GSL-deficient purple radish pigment | 88.40 | 25.31 | −7.08 |
| Sample 2 (product of Example) | 4MTBG-GSL-deficient red radish pigment | 91.04 | 20.11 | 0.92 |
| Sample 3 (comparative product) | Wild-type purple radish pigment | 88.31 | 25.19 | −7.36 |
| Sample 4 (comparative product) | Wild-type red radish pigment | 91.04 | 19.97 | 0.12 |
| Sample 5 (commercially available product) | Purple sweet potato pigment | 88.39 | 24.89 | −6.41 |
| Sample 6 (commercially available product) | Grape juice pigment | 84.39 | 16.69 | 0.04 |
| Sample 7 (commercially available product) | Grape skin pigment | 84.00 | 16.55 | −0.37 |
| Sample 8 (commercially available product) | Elderberry pigment | 90.04 | 19.37 | 2.67 |
| Sample 9 (commercially available product) | Purple corn pigment | 89.66 | 16.83 | 2.81 |

(2) Evaluation of Color

Figure 5:
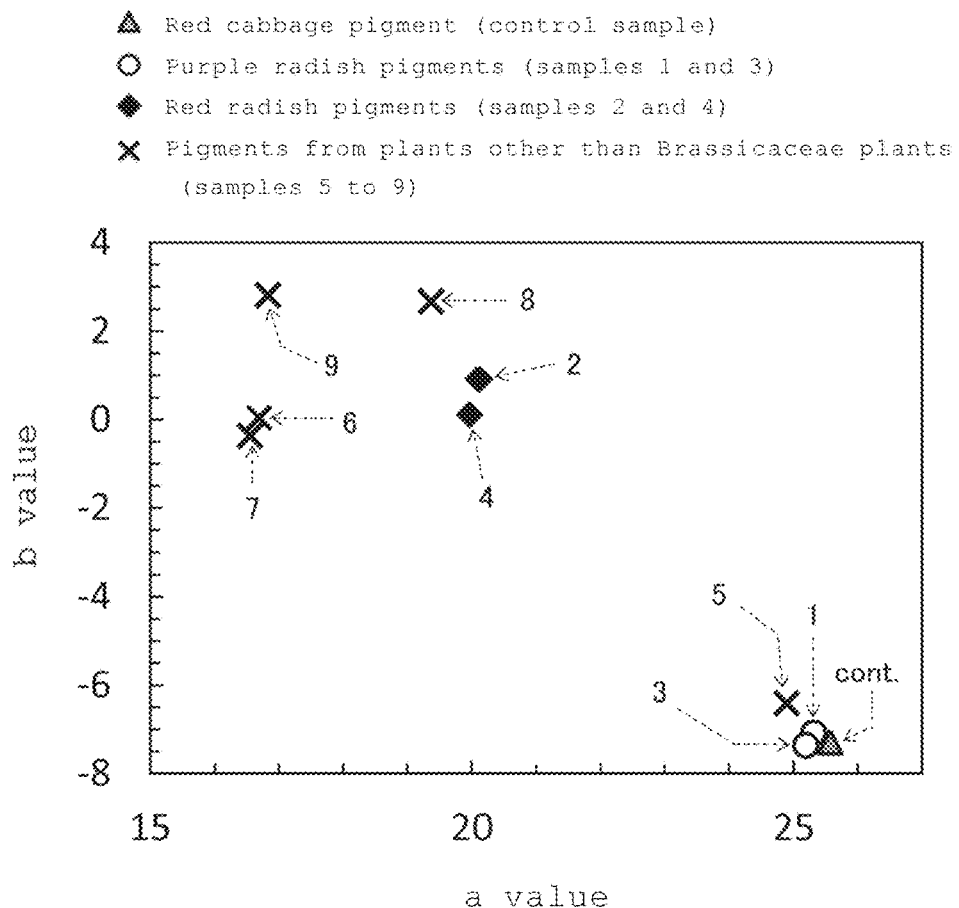
FIG. 5 is a graph in which the hue of each anthocyanin pigment preparation is plotted on a- and b-axis rectangular coordinates in the Hunter Lab color system in the color analysis of the pigment preparations in Example 3. The numbers in FIG. 5 indicate sample numbers.

Based on the values described above, lightness, chroma, and hue were evaluated according to the method described in Example 2. "Lightness" was evaluated using an L value. "Chroma" was evaluated using a chroma value calculated according to (Equation 2) described above. "Hue" was evaluated by calculating a hue value. Hues were plotted on a- and b-axis rectangular coordinates to prepare a graph that shows the relationship with the hue of the red cabbage pigment (control sample) (FIG. 5). In addition, each sample (4MTB-GSL-deficient colored radish pigment) was compared with the red cabbage pigment (control sample), and the color difference between the two (distance between two colors), which is indicated by a ΔE value, was calculated using (Equation 3) described above. Table 12 shows the results.

Color comparisons between the anthocyanin pigment preparations based on the obtained analysis results revealed that the pigments from purple radishes (samples 1 and 3) exhibited a slightly reddish red-purple color at a pH of 3.0 and exhibited color very similar to that of the red cabbage pigment (control sample) in all of hue, chroma, and lightness. The purple radish pigments had color characteristics closer to those of the red cabbage pigment than the purple sweet potato pigment (sample 5: a pigment that has been considered as an alternative to red cabbage pigment).

On the other hand, the pigments from red radishes (samples 2 and 4) exhibited a slightly purplish bright-red color (it also appeared slightly orange to the naked eye) at a pH of 3.0, and had a color slightly closer to that of the elderberry pigment (sample 8).

The above results showed that the pigment preparations of the present invention (samples 1 and 2) can exhibit color in a wide range from slightly reddish red-purple to a slightly purplish bright-red color at a pH of 3.0.

TABLE 12

| Sample | Pigment name | Lightness (L value) | Chroma (chroma value) | Hue (hue value) | Color difference (ΔE value) |
|---|---|---|---|---|---|
| Control sample (commercially available product) | Red cabbage pigment | 87.48 | 26.59 | 5.6RP | — |
| Sample 1 (product; of Example) | 4MTBG-GSL-deficient purple radish pigment | 88.40 | 26.28 | 5.7RP | 0.98 |
| Sample 2 (product of Example) | 4MTBG-GSL-deficient red radish pigment | 91.04 | 20.13 | 0.7R | 10.48 |
| Sample 3 (comparative product) | Wild-type purple radish pigment | 88.31 | 26.24 | 5.5RP | 0.92 |
| Sample 4 (comparative product) | Wild-type red radish pigment | 91.04 | 19.97 | 0.1R | 9.95 |
| Sample 5 (commercially available product) | Purple sweet potato pigment | 88.39 | 25.70 | 6.0RP | 1.44 |
| Sample 6 (commercially available product) | Grape juice pigment | 84.39 | 16.69 | 0.0R | 11.92 |
| Sample 7 (commercially available product) | Grape skin pigment | 84.00 | 16.55 | 9.6RP | 11.89 |
| Sample 8 (commercially available product) | Elderberry pigment | 90.04 | 19.55 | 2.2R | 12.01 |
| Sample 9 (commercially available product) | Purple corn pigment | 89.66 | 17.06 | 2.6R | 13.53 |

Example 4

Evaluation of Smell Components of Pigment Preparations

The amounts and proportions of the smell components of the 4MTB-GSL-deficient colored radish pigment preparations prepared in Example 1 were analyzed and compared with those of common wild-type colored radish pigments and red cabbage pigment. In addition, the amounts and proportions of the smell components generated after long-term storage at high temperature were examined to investigate changes in the smell components over time.

(1) GC/MS Analysis of Smell Components

For each pigment preparation, a test liquid containing the pigment preparation, 0.2% (w/w) citric acid, 20% (w/w) ethanol, and water was prepared so as to have a color value $E^{10\%}_{1cm}$ of 10. As a control sample, a commercially available red cabbage pigment preparation (produced by San-Ei Gen F.F.I., Inc.) was used.

1.0 mL of each test liquid was individually sealed in 20-mL vials. The vials were stored in the dark at 50° C. for 5 days. Further, as a control test, the vials were stored in the dark at a temperature as low as 5° C. for 5 days.

After storage, each vial was maintained in a thermostatic bath at 40° C. for 30 minutes, the smell components in the headspace of the vial were collected with an SPME fiber (PDMS/DVB) for 30 minutes while maintaining the vial at 40° C., and GC/MS analysis was performed. The conditions for maintaining the vial (maintaining at 40° C. for 30 minutes) are conditions in which the vapor pressure of each smell component shown in Tables 13 to 17 reaches saturated vapor pressure.

The GC/MS analysis was performed using a gas chromatograph mass spectrometer (Agilent 7890a/5975C produced by Agilent Technologies) and an analytical column (DB-WAX, 60 m×0.25 mm id, produced by Agilent Technologies). The analysis was conducted under the following oven temperature conditions: 50° C. for 2 minutes, and then from 50° C. to 220° C. at a rising gradient of 3° C./minute.

From the obtained spectra, the six main smell components of the Brassicaceae plant pigments (the components shown in the following tables) were identified, and the peak areas of the components were calculated. Tables 13 to 17 below show the results.

TABLE 13

| | Red cabbage pigment (control sample: commercially available product) | Peak area (×10³) | |
|---|---|---|---|
| | | Storage at 5° C. (low temperature) | Storage at 50° C. (high temperature) |
| Component A | Methyl mercaptan | 64 | 81 |
| Component B | Dimethyl disulfide | 0 | 122 |
| Component C | Dimethyl trisulfide | 164 | 295 |
| Component D | Nonanal | 53 | 81 |
| Component E | Ethyl octanoate | 354 | 1019 |
| Component F | 5-methylthiopentanenitrile | 13529 | 9863 |

TABLE 14

| | 4MTB-GSL-deficient purple radish pigment (sample 1: product of Example) | Peak area (×10³) | |
|---|---|---|---|
| | | Storage at 5° C. (low temperature) | Storage at 50° C. (high temperature) |
| Component A | Methyl mercaptan | 30 | 41 |
| Component B | Dimethyl disulfide | 0 | 0 |

TABLE 14-continued

|  |  | Peak area (×10³) | |
| --- | --- | --- | --- |
| 4MTB-GSL-deficient purple radish pigment (sample 1: product of Example) | | Storage at 5° C. (low temperature) | Storage at 50° C. (high temperature) |
| Component C | Dimethyl trisulfide | 0 | 0 |
| Component D | Nonanal | 605 | 480 |
| Component E | Ethyl octanoate | 85 | 1040 |
| Component F | 5-methylthiopentanenitrile | 424 | 1177 |

TABLE 15

|  |  | Peak area (×10³) | |
| --- | --- | --- | --- |
| 4MTB-GSL-deficient red radish pigment (sample 2: product of Example) | | Storage at 5° C. (low temperature) | Storage at 50° C. (high temperature) |
| Component A | Methyl mercaptan | 30 | 49 |
| Component B | Dimethyl disulfide | 0 | 0 |
| Component C | Dimethyl trisulfide | 0 | 0 |
| Component D | Nonanal | 790 | 462 |
| Component E | Ethyl octanoate | 242 | 977 |
| Component F | 5-methylthiopentanenitrile | 280 | 3631 |

TABLE 16

|  |  | Peak area (×10³) | |
| --- | --- | --- | --- |
| Wild-type purple radish pigment (sample 3: comparative product) | | Storage at 5° C. (low temperature) | Storage at 50° C. (high temperature) |
| Component A | Methyl mercaptan | 1282 | 1796 |
| Component B | Dimethyl disulfide | 20487 | 509101 |
| Component C | Dimethyl trisulfide | 28355 | 549259 |
| Component D | Nonanal | 812 | 522 |
| Component E | Ethyl octanoate | 209 | 2281 |
| Component F | 5-methylthiopentanenitrile | 29925 | 28763 |

TABLE 17

|  |  | Peak area (×10³) | |
| --- | --- | --- | --- |
| Wild-type red radish pigment (sample 4: comparative product) | | Storage at 5° C. (low temperature) | Storage at 50° C. (high temperature) |
| Component A | Methyl mercaptan | 1328 | 2075 |
| Component B | Dimethyl disulfide | 40029 | 260161 |
| Component C | Dimethyl trisulfide | 56722 | 427935 |
| Component D | Nonanal | 755 | 354 |
| Component E | Ethyl octanoate | 133 | 1832 |
| Component F | 5-methylthiopentanenitrile | 136441 | 128564 |

(2) Analysis of Odor Components

Among the detected main smell components of the Brassicaceae plants, the absolute amounts of the "sulfur odor components" were quantified for analysis of odor components. A series of diluted test liquids (0 ppm, 0.1 ppm, 1 ppm, 10 ppm, and 100 ppm) of commercially available reagents, i.e., methyl mercaptan standard (produced by Wako Pure Chemical Industries, Ltd.), dimethyl disulfide standard (produced by Wako Pure Chemical Industries, Ltd.), and dimethyl trisulfide standard (produced by Wako Pure Chemical Industries, Ltd.), were prepared. A fixed amount (5 µL) of each test liquid was directly injected into a gas chromatograph mass spectrometer (Agilent 7890a/5975C produced by Agilent Technologies) to perform GC/MS analysis. The peak doses of the series of diluted test liquids when the split ratio was set to 1:20 were 0 ng, 0.024 ng, 0.238 ng, 2.381 ng, and 23.810 ng. From the obtained peak area of each substance, a calibration curve was prepared for each substance.

As a result, the calibration curve equations shown in Table 18 were obtained. It was confirmed that the square of the correlation coefficient ($R^2$) in each equation was 1.0, indicating that there was a positive correlation between the mass (x) and the peak area (y).

In each equation, "x" represents the mass (ng) of the compound contained in the gas in the sealed space of the headspace (19 mL), and "y" represents the peak area.

TABLE 18

|  |  | Calibration curve equation | $R^2$ |
| --- | --- | --- | --- |
| Component A | Methyl mercaptan | y = 539.12x | 1.0 |
| Component B | Dimethyl disulfide | y = 1727.8x | 1.0 |
| Component C | Dimethyl trisulfide | y = 1886.2x | 1.0 |

Using the calibration curves, the concentrations of the sulfur odor components in the headspace (19 mL in the 20-mL vial) were calculated from the peak area values (Tables 19 to 21). In addition, the total amount of the sulfur odor components was also calculated (Table 22 and FIG. 6(A)). Since the values of the vertical axis of the wild-type colored radish pigments (samples 3 and 4) were orders of magnitude higher, these samples were omitted from FIG. 6.

The results showed that the amounts of methyl mercaptan, dimethyl disulfide, and dimethyl trisulfide, which cause sulfur odor, present in the gas in the sealed space were smaller in the 4MTB-GSL-deficient colored radish pigment preparations (samples 1 and 2) than in the control red cabbage pigment (commercially available product (purified)). In particular, dimethyl disulfide and dimethyl trisulfide, which are components causing stuffy odor, were below the detection limit of GC/MS analysis, and no generation of the components was confirmed (Tables 20 and 21).

In addition, the total amount of the sulfur odor components in the headspace (19 mL in the 20-mL vial) did not exceed even 5 pg/mL (Table 22 and FIG. 6(A)).

These facts indicated that each of the 4MTB-GSL-deficient colored radish pigment preparations (samples 1 and 2) had a component composition such that generation of sulfur odor was significantly suppressed, in particular, stuffy odor was much less likely to be generated.

The amounts of these components in the wild-type colored radish pigments (samples 3 and 4) were orders of magnitude higher than those in the 4MTB-GSL-deficient colored radish pigment preparations (samples 1 and 2) and the red cabbage pigment (control sample) (Tables 19 to 22).

TABLE 19

|  |  | Concentration in the headspace (pg/mL) | |
| --- | --- | --- | --- |
| Methyl mercaptan (component A) | | Storage at 5° C. (low temperature) | Storage at 50° C. (high temperature) |
| Control sample | Red cabbage pigment (commercially available product) | 6.55 | 7.90 |

TABLE 19-continued

| | Methyl mercaptan (component A) | Concentration in the headspace (pg/mL) | |
|---|---|---|---|
| | | Storage at 5° C. (low temperature) | Storage at 50° C. (high temperature) |
| Sample 1 (product of Example) | 4MTBG-GSL-deficient purple radish pigment | 2.89 | 3.97 |
| Sample 2 (product of Example) | 4MTBG-GSL-deficient red radish pigment | 2.94 | 4.83 |
| Sample 3 (comparative raw material) | Wild-type purple radish pigment | 125.15 | 175.37 |
| Sample 4 (comparative raw material) | Wild-type red radish pigment | 129.60 | 202.61 |

TABLE 20

| | Dimethyl disulfide (component B) | Concentration in the headspace (pg/mL) | |
|---|---|---|---|
| | | Storage at 5° C. (low temperature) | Storage at 50° C. (high temperature) |
| Control sample (commercially available product) | Red cabbage pigment | 0.00 | 3.72 |
| Sample 1 (product of Example) | 4MTBG-GSL-deficient purple radish pigment | 0.00 | 0.00 |
| Sample 2 (product of Example) | 4MTBG-GSL-deficient red radish pigment | 0.00 | 0.00 |
| Sample 3 (comparative raw material) | Wild-type purple radish pigment | 624.45 | 15517.93 |
| Sample 4 (comparative raw material) | Wild-type red radish pigment | 1220.12 | 7929.96 |

TABLE 21

| | Dimethyl trisulfide (component C) | Concentration in the headspace (pg/mL) | |
|---|---|---|---|
| | | Storage at 5° C. (low temperature) | Storage at 50° C. (high temperature) |
| Control sample (commercilly available product) | Red cabbage pigment | 4.59 | 8.23 |
| Sample 1 (product of Example) | 4MTBG-GSL-deficient purple radish pigment | 0.00 | 0.00 |
| Sample 2 (product of Example) | 4MTBG-GSL-deficient red radish pigment | 0.00 | 0.00 |
| Sample 3 (comparative raw material) | Wild-type purple radish pigment | 791.20 | 15326.24 |
| Sample 4 (comparative raw material) | Wild-type red radish pigment | 1582.75 | 11940.89 |

TABLE 22

| | Total of sulfur odor components (A + B + C) | Concentration in the headspace (pg/mL) | |
|---|---|---|---|
| | | Storage at 5° C. (low temperature) | Storage at 50° C. (high temperature) |
| Control sample (commercially available product) | Red cabbage pigment | 11.13 | 19.86 |
| Sample 1 (product of Example) | 4MTBG-GSL-deficient purple radish pigment | 2.89 | 3.97 |
| Sample 2 (product of Example) | 4MTBG-GSL-deficient red radish pigment | 2.94 | 4.83 |
| Sample 3 (comparative raw material) | Wild-type purple radish pigment | 1540.80 | 31019.54 |
| Sample 4 (comparative raw material) | Wild-type red radish pigment | 2932.47 | 20073.46 |

(3) Analysis and Evaluation of Odor Characteristics

Figure 6:
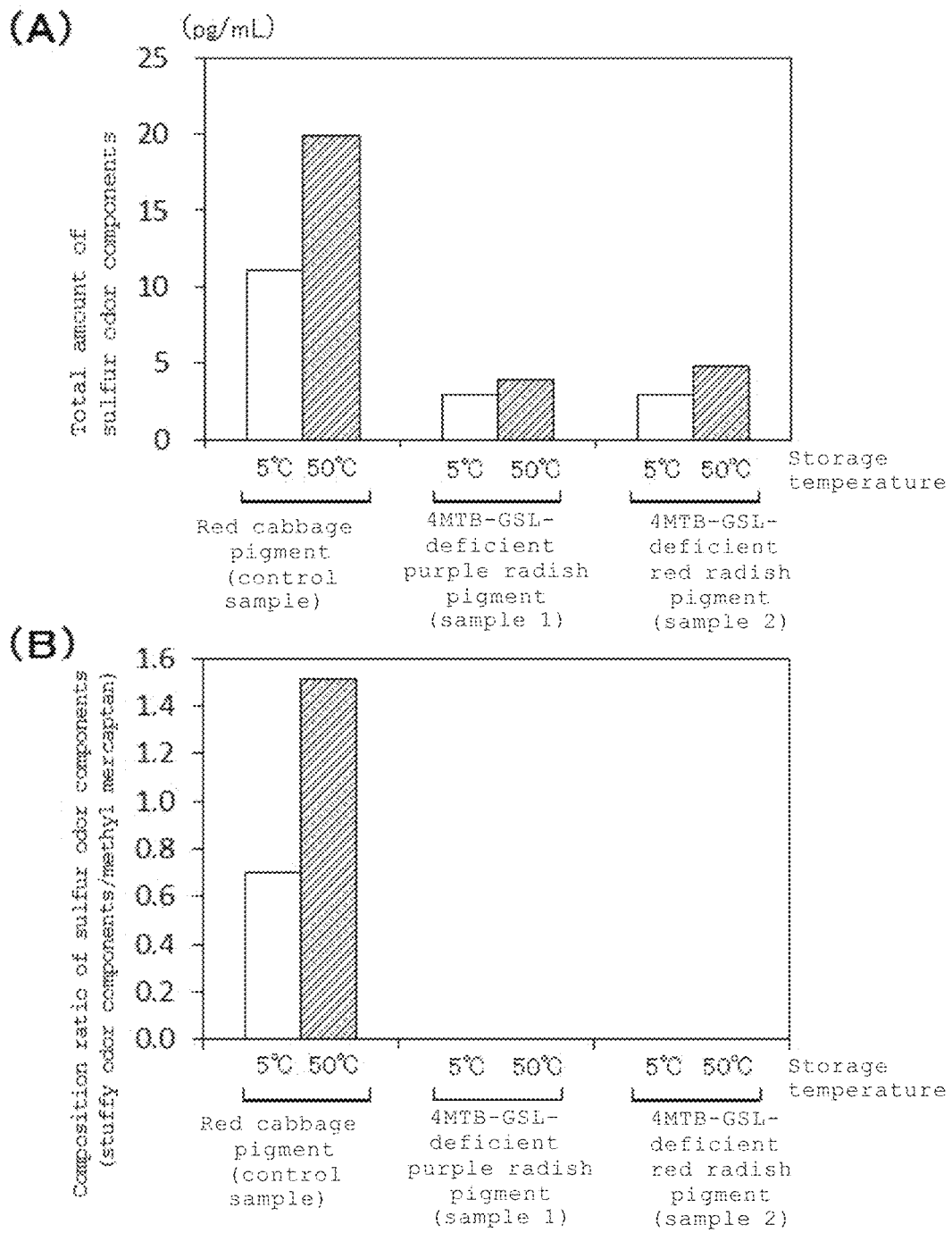
FIG. 6 shows graphs indicating the amounts of the sulfur odor components and the composition ratio in each pigment preparation in the analysis of the odor components of the pigment preparations in Example 4. (A): Graph showing the total amount of the sulfur odor components (methyl mercaptan, dimethyl disulfide, and dimethyl trisulfide) in the headspace of the vial. (B): Graph showing the ratio of the total mass of dimethyl disulfide and dimethyl trisulfide, which are stuffy odor components, to the mass of methyl mercaptan.

To investigate the "odor characteristics" (odor properties) of the 4MTB-GSL-deficient colored radish pigment preparations (samples 1 and 2), the composition ratio of the total amount of "dimethyl disulfide (component B)" and "dimethyl trisulfide (component C)" generated, which are components causing "stuffy odor," to the amount of "methyl mercaptan (component A)" generated ((B+C)/A) was calculated (Table 23 and FIG. 6(B)). When the value of this ratio is low in a pigment preparation, the pigment preparation is believed to have an odor component composition in which stuffy odor is less likely to be perceived. (Note that since the values of the vertical axis of the wild-type colored radish pigments (samples 3 and 4) were orders of magnitude higher, these samples were omitted from the graph of FIG. 6.)

As shown in the analysis results of Item (2) above, in the 4MTB-GSL-deficient colored radish pigment preparations (samples 1 and 2), dimethyl disulfide and dimethyl trisulfide were below the detection limit of GC/MS analysis, and no generation of the components was confirmed (Tables 20 and 21). As is clear from this fact, the sulfur odor component composition ratio in each of the pigments (samples 1 and 2) is such that the amounts of dimethyl disulfide and dimethyl trisulfide were zero relative to the amount of methyl mercaptan (Table 23 and FIG. 6(B)). In addition, this value remained at 0 after storage at 50° C. (high temperature) for 5 days.

In contrast, in the red cabbage pigment (control sample), dimethyl disulfide and dimethyl trisulfide were generated in an amount 0.7 times the mass of methyl mercaptan. Further, the ratio was increased to 1.51 after storage at 50° C. (high temperature) for 5 days (Table 23 and FIG. 6(B)).

These results showed that the 4MTBG-GSL-deficient colored radish pigment preparations (samples 1 and 2) are pigment compositions with odor characteristics (odor properties) such that "stuffy odor" is much less likely to be generated. These pigment compositions are believed to have an odor component composition in which "stuffy odor" is much less likely to be generated, even when the color value is increased.

The values of this ratio in the wild-type colored radish pigments (samples 3 and 4) were orders of magnitude higher than those of the 4MTB-GSL-deficient colored radish pigment preparations (samples 1 and 2) and the red cabbage pigment (control sample) (Table 23).

TABLE 23

| Sulfur odor composition ratio | | Composition ratio ((B + C)/A) | |
|---|---|---|---|
| | | Storage at 5° C. (low temperature) | Storage at 50° C. (high temperature) |
| Control sample (commercially available product) | Red cabbage pigment | 0.70 | 1.51 |
| Sample 1 (product of Example) | 4MTPG-GSL-deficient purple radish pigment | 0.00 | 0.00 |
| Sample 2 (product of Example) | 4MTBG-GSL-deficient red radish pigment | 0.00 | 0.00 |
| Sample 3 (comparative raw material) | Wild-type purple radish pigment | 11.31 | 175.89 |
| Sample 4 (comparative raw material) | Wild-type red radish pigment | 21.63 | 98.07 |

(4) Evaluation of Return Smell

It was clear from an preliminary experiment that changes in the smell components over time were suppressed in the test liquids after storage in the dark at 5° C. (low temperature). Thus, in the analysis of (1) to (3) above, the "analysis values after storage in the dark at 5° C. (low temperature)" were regarded as "analysis values of the test liquids before storage," and evaluation of "return smell" during storage at high temperature was performed by comparing the "analysis values after storage in the dark at 5° C. (low temperature)" with the "measurement values of the test liquids after storage in the dark at 50° C. (high temperature)."

As shown in the analysis results described above, the results revealed that the sulfur odor components in the 4MTB-GSL-deficient colored radish pigment preparations (samples 1 and 2) did not appreciably increase, even after storage at 50° C. for 5 days. Moreover, the total amount of the sulfur odor components in the headspace (19 mL in 20-mL vial) did not exceed even 5 pg/mL (Table 22 and FIG. 6(A)).

Additionally, the pigments (samples 1 and 2) were free of dimethyl disulfide and dimethyl trisulfide even after storage at 50° C. (high temperature) for 5 days, indicating that generation of the components causing stuffy odor was significantly suppressed (Tables 20, 21, and 23, and FIG. 6(B)).

In contrast, in the red cabbage pigment (control sample: commercially available product), generation of the sulfur odor components increased approximately two-fold after storage at 50° C. for 5 days, even though it was a commercially available purified product (Table 22 and FIG. 6(A)). Further, in the odor component composition, the proportion of the total amount of dimethyl disulfide and dimethyl trisulfide increased more than two-fold (Table 23 and FIG. 6(B)), indicating that the amounts of the components causing stuffy odor significantly increased after storage at high temperature in the red cabbage pigment (control sample).

The above results showed that the 4MTB-GSL-deficient colored radish pigment preparations (samples 1 and 2) had a component composition in which generation of "return smell" was significantly suppressed even after long-term storage at high temperature, in particular, generation of the return smell of "stuffy odor" was significantly suppressed. It was confirmed that this effect cannot be achieved even with the commercially available product of red cabbage pigment (control sample (purified product)) whose odor has been considered relatively favorable.

(5) Analysis and Evaluation of Smell Characteristics

To investigate the "smell characteristics" (smell properties) of the 4MTB-GSL-deficient colored radish pigment preparations (samples 1 and 2), the ratio of the peak area of "5-methylthiopentanenitrile (component F)" to the peak areas of "methyl mercaptan, dimethyl disulfide, and dimethyl trisulfide (components A+B+C)" was calculated, focusing on "5-methylthiopentanenitrile (component F)," which is a substance causing the "rapeseed-like smell" of red cabbage pigment (Table 24). The ratios were compared to evaluate whether the smell characteristics of the pigment preparations were of the same quality as those of red cabbage pigment. This peak area ratio does not refer to the mass ratio of the smell components generated from the pigment preparation, and is a relative index that is comparable between the samples.

The results showed that in the 4MTB-GSL-deficient colored radish pigment preparations (samples 1 and 2), the peak area ratio of 5-methylthiopentanenitrile (component F) to the components causing sulfur odor was in the range of 9.33 to 74.1, which was similar to that of the red cabbage pigment (control sample) (19.8 to 59.33). Specifically, it was confirmed that the pigment preparations according to the present invention had a smell component composition ratio similar to that of the red cabbage pigment.

In contrast, in the wild-type colored radish pigments (samples 3 and 4), the peak area ratio (0.03 to 1.39) was very small, thus confirming that the wild-type colored radish pigments had a smell component composition ratio that was completely different from that of the red cabbage pigment.

TABLE 24

| Rapeseed-like smell component/sulfur odor components (relative value) | | Peak area ratio (F/(A + B + C)) | |
|---|---|---|---|
| | | Storage at 5° C. (low temperature) | Storage at 50° C. (high temperature) |
| Control sample (commercial available product) | Ped cabbage pigment | 59.33 | 19.80 |
| Sample 1 (product of Example) | 4MTBG-GSL-deficient purple radish pigment | 14.13 | 28.71 |
| Sample 2 (product of Example) | 4MTBG-GSL-deficient red radish pigment | 9.33 | 74.10 |
| Sample 3 (comparative product) | Wild-type purple radish pigment | 0.60 | 0.03 |
| Sample 4 (comparative product) | Wild-type red radish pigment | 1.39 | 0.19 |

Example 5

Production and Stability Evaluation of Beverages

Beverages were prepared using the 4MTB-GSL-deficient colored radish pigment preparations prepared in Example 1, and the light stability and heat stability of the beverages were evaluated.

(1) Preparation of Beverages

Beverages were prepared such that the Brix was 100 (high-fructose corn syrup Brix 750: 13.3% (w/v)), the pH was 3.0 (adjusted to a pH of 3.0 with citric acid anhydride: 0.2% (w/v) and trisodium citrate), and each pigment preparation was individually added in an amount of 0.03% (w/w) in terms of a color value $E^{10\%}_{1cm}$ of 80. These were sterilized by heating to 93° C., and hot-packed in 200-mL PET bottles. The obtained PET bottle beverages were used as test liquids.

(2) Light Resistance Test

The remaining anthocyanin pigment percentage under irradiation with fluorescent light was measured to evaluate the light stability of the pigment preparations.

Stability Test

The test liquids in the PET bottles were irradiated with white fluorescent light of 10000 Lux using a fluorescent light irradiation device at 20° C. for 5 days. A CLH-301 (produced by Tomy Seiko Co. Ltd.) cultivation chamber was used as the fluorescent light irradiation device.

Control Test

As a control test, the test liquids were stored in the dark at a temperature as low as 5° C. for 5 days.

Evaluation of Light Resistance of Pigment Preparations

Figure 7:
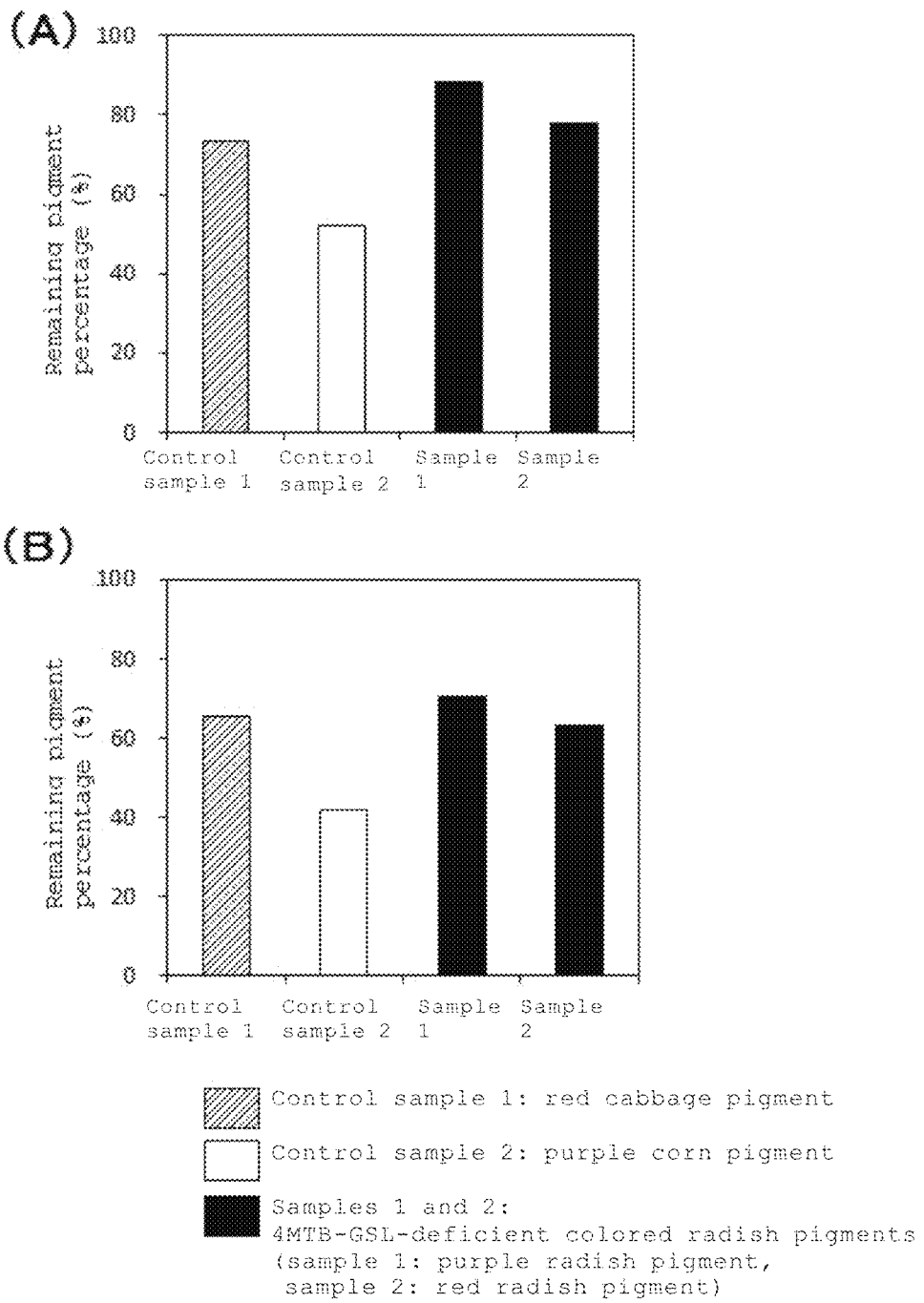
FIG. 7 shows graphs indicating the remaining pigment percentage in each pigment preparation after the stability test of each pigment preparation in Example 5. (A): Graph showing the remaining pigment percentage after storage for 5 days at 10000 Lux. (B): Graph showing the remaining pigment percentage after storage for 5 days at 50° C. (in the dark).

After storage, colorimetry was performed by measuring transmitted light at measurement wavelengths of 380 to 780 nm using a spectrophotometer (V-560 produced by JASCO Corporation; optical path length of measurement cell: 1 cm) to calculate the remaining anthocyanin pigment percentage according to the following (Equation 4). Table 25 and FIG. 7 (A) show the results.

$$\text{Remaining pigment percentage}(\%) = \frac{\text{Absorbance at maximum absorption wavelength after stability test}}{\text{Absorbance at maximum absorption wavelength after control test}} \times 100 \quad \text{(Equation 4)}$$

The results indicated that the 4MTB-GSL-deficient colored radish pigment preparations (samples 1 and 2) each showed a high remaining pigment percentage similar to that of the red cabbage pigment (control sample 1), even when they were added to beverages and irradiated with intense light of 10000 Lux for a long period of time. As can be seen from this fact, the 4MTB-GSL-deficient colored radish pigment preparations (samples 1 and 2) had high resistance to light.

The light intensity in the irradiation of the test, i.e., 10000 Lux, is five to ten times the light intensity of fluorescent lamps used in usual retail stores etc.

TABLE 25

| | Light resistance test | Remaining pigment percentage (%) |
|---|---|---|
| Control sample 1 (commercially available product) | Red cabbage pigment | 73.2 |
| Control sample 2 (commercially available product) | Purple corn pigment | 52.2 |
| Sample 1 (product of Example) | 4MTBG-GSL-deficient purple radish pigment | 88.2 |

TABLE 25-continued

| | Light resistance test | Remaining pigment percentage (%) |
|---|---|---|
| Sample 2 (product of Example) | 4MTBG-GSL-deficient red radish pigment | 78.0 |

(3) Heat Resistance Test

The heat stability of the pigment preparations was evaluated by measuring the remaining anthocyanin pigment percentage under high-temperature storage conditions.

The test liquids in PET bottles prepared in Item (1) above were stored in the dark at a temperature as high as 50° C. for 5 days, and the remaining anthocyanin pigment percentage was calculated in the same manner as described in Item (2) above. In addition, samples obtained by storing the test liquids in the dark at a temperature as low as 5° C. for 5 days were used for a control test. Table 26 and FIG. 7 (B) show the results.

The results indicated that the 4MTB-GSL-deficient colored radish pigment preparations (samples 1 and 2) each showed a remaining pigment percentage similar to that of the red cabbage pigment (control sample 1) even when they were added to beverages and stored at a temperature as high as 50° C. for a long period of time. As can be seen from this fact, the 4MTB-GSL-deficient colored radish pigment preparations (samples 1 and 2) had high resistance to heat.

At the temperature in the test, i.e., 50° C., a chemical reaction proceeds approximately eight times faster than when stored at 20° C., which is a typical room temperature.

TABLE 26

| | Heat resistance test | Remaining pigment percentage (%) |
|---|---|---|
| Control sample 1 (commercially available product) | Red cabbage pigment | 65.6 |
| Control sample 2 (commercially available product) | Purple corn pigment | 41.6 |
| Sample 1 (product of Example) | 4MTBG-GSL-deficient purple radish pigment | 70.2 |
| Sample 2 (product of Example) | 4MTBG-GSL-deficient red radish pigment | 63.2 |

Example 6

Sensory Evaluation of Beverages

Colored beverages were prepared as products, and sensory evaluation of flavor (smell and taste) was performed.

(1) Forced Deterioration Treatment

Beverages individually containing each pigment preparation were prepared and stored for 5 days while exposed to irradiation with light of 10000 Lux or a temperature as high as 50° C. The basic operation process and conditions for preparation of beverages and deterioration treatment were the same as those in the method described in Example 5. As another treatment, the beverages were stored in the dark at a temperature as low as 5° C. for 5 days.

(2) Sensory Evaluation of Flavor

Sensory evaluation of flavor of the beverages was performed in a blind manner by four panelists who routinely do flavor determination. The intensity of smell (smell intensity)

of the beverages was determined according to the following criteria. Tables 27 to 29 showed the results.

Criteria for Determining Smell Intensity

The smell intensity was evaluated based on a five-point scale of −<+<++<+++<++++ according to the odor intensity: "−"=no odor and "++++"=strongest odor (sulfur odor).

The results demonstrated that the beverages produced using the 4MTB-GSL-deficient colored radish pigment preparations (samples 1 and 2) had very little smell and were free of problematic "sulfur odor" (Table 27). Further, even after the deterioration treatment under light irradiation or high-temperature conditions for 5 days, the beverages underwent slight odor generation, and no generation of "stuffy odor" was confirmed (Tables 28 and 29).

In this regard, the red cabbage pigment (commercially available product) used as a control sample, which is highly purified, had significantly reduced odor; however, clear generation of return smell (sulfur odor) was confirmed after the deterioration treatment under light irradiation or high-temperature conditions.

On the other hand, the beverage produced by adding the wild-type colored radish pigment (sample 3) had strong "sulfur odor" (Table 27). Further, "sulfur odor," in particular, "stuffy odor" was further increased by the deterioration treatment for 5 days, and particularly strong "stuffy odor" was confirmed after high-temperature storage (Tables 28 and 29).

TABLE 27

| Storage in the dark at low temperature | | Smell intensity | Notes |
|---|---|---|---|
| Control sample (commercially available product) | Red cabbage pigment | − | The smell itself was slight, without sulfur odor or stuffy odor. |
| Sample 1 (product of Example) | 4MTBG-GSL-deficient purple radish pigment | − | The smell itself was slight, without sulfur odor or stuffy odor. |
| Sample 2 (product of Example) | 4MTBG-GSL deficient red radish pigment | − | The smell itself was slight, without sulfur odor or stuffy odor. |
| Sample 3 (comparative product) | Wild-type purple radish pigment | +++ | There was a very strong sulfur odor and stuffy odor. |

TABLE 28

| Storage under light irradiation | | Smell intensity | Notes |
|---|---|---|---|
| Control sample (commercially available product) | Red cabbage pigment | ++ | There was a higher-fatty-acid-like heavy fermentation flavor, with a slight sulfur odor like eggs. |
| Sample 1 (product of Example) | 4MTBG-GSL-deficient purple radish pigment | + | The smell itself was slight. There was a higher-fatty-acid-like heavy fermentation flavor. A slight odor was perceived. |

TABLE 28-continued

| Storage under light irradiation | | Smell intensity | Notes |
|---|---|---|---|
| Sample 2 (product of Example) | 4MTBG-GSL-deficient red radish pigment | + | The smell itself was slight. There was a higher-fatty-acid-like heavy fermentation flavor. A slight odor was perceived. |
| Sample 3 (comparative product) | Wild-type purple radish pigment | ++++ | There was a strong top note with fermentation flavor. A strong stuffy odor was perceived. |

TABLE 29

| Storage at high temperature | | Smell intensity | Notes |
|---|---|---|---|
| Control sample (commercially available product) | Red cabbage pigment | ++ | There was a scent accompanied by sweetness. A sulfur odor was perceived. |
| Sample 1 (product of Example) | 4MTBG-GSL-deficient purple radish pigment | + | The smell itself was slight. There was a scent accompanied by sweetness. A slight odor was perceived. |
| Sample 2 (product of Example) | 4MTBG-GSL-deficient red radish pigment | + | The smell itself was slight. There was a scent accompanied by sweetness. A slight odor was perceived. |
| Sample 3 (comparative product) | Wild-type purple radish pigment | ++++ | The smell was the strongest stuffy odor, accompanied by slight sweetness. |

DESCRIPTION OF REFERENCE NUMERALS 1. 4MTB-GSL deficient purple colored radish
2. 4MTB-GSL deficient red colored radish

The invention claimed is:

1. A method for producing an anthocyanin pigment preparation, comprising extracting an anthocyanin pigment from an anthocyanin-pigment-containing colored radish exhibiting 4-methylthio-3-butenyl glucosinolate deficiency.

2. A method for producing an anthocyanin pigment preparation, comprising squeezing juice from an anthocyanin-pigment-containing colored radish exhibiting 4-methylthio-3-butenyl glucosinolate deficiency.

3. The method according to claim 2, further comprising:
crossing a white radish exhibiting the 4-methylthio-3-butenyl glucosinolate deficiency with an anthocyanin-pigment-containing colored radish, and acquiring the anthocyanin-pigment-containing colored radish exhibiting the 4-methylthio-3-butenyl glucosinolate deficiency; and
crossing the anthocyanin-pigment-containing colored radish exhibiting the 4-methylthio-3-butenyl glucosinolate deficiency with an anthocyanin-pigment-containing colored radish inbred line and selecting a colored radish having a high color value and the 4-methylthio-3-butenyl glucosinolate deficiency.

* * * * *

UNITED STATES PATENT AND TRADEMARK OFFICE
CERTIFICATE OF CORRECTION

PATENT NO. : 11,352,501 B2  
APPLICATION NO. : 15/506587  
DATED : June 7, 2022  
INVENTOR(S) : Masahiko Ishida et al.

Page 1 of 1

It is certified that error appears in the above-identified patent and that said Letters Patent is hereby corrected as shown below:

On the Title Page

Item (72)

Delete "(72) Inventors: "Masahiko Ishida, Tsu (JP); Takayoshi Ohara, Tsu (JP); Nobuko Fukino, Tsu (JP); Tomohiro Kakizaki, Tsu (JP); Tomomichi Ohno, Tsu (JP); Koji Hamasaki, Toyonaka (JP); Takamasa Yokoyama, Toyonaka (JP); Masashi Imai, Toyonaka (JP)"

Insert --(72) Inventors: Masahiko Ishida, Tsukuba (JP); Takayoshi Ohara, Tsu (JP); Nobuko Fukino, Tsu (JP); Tomohiro Kakizaki, Tsu (JP); Tomomichi Ohno, Toyonaka (JP); Koji Hamasaki, Toyonaka (JP); Takamasa Yokoyama, Toyonaka (JP); Masashi Imai, Toyonaka (JP)--

Signed and Sealed this  
Sixth Day of September, 2022

Katherine Kelly Vidal  
*Director of the United States Patent and Trademark Office*